(12) United States Patent
Wilson et al.

(10) Patent No.: US 11,877,767 B2
(45) Date of Patent: *Jan. 23, 2024

(54) INTRALUMINAL TISSUE MODIFYING SYSTEMS AND ASSOCIATED DEVICES AND METHODS

(71) Applicant: INTERVENE, INC., South San Francisco, CA (US)

(72) Inventors: Fletcher T. Wilson, San Francisco, CA (US); David Batten, Los Gatos, CA (US); Benjamin J. Clark, Redwood City, CA (US); Michi E. Garrison, Half Moon Bay, CA (US)

(73) Assignee: INTERVENE, INC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/559,899

(22) Filed: Dec. 22, 2021

(65) Prior Publication Data
US 2022/0346827 A1 Nov. 3, 2022

Related U.S. Application Data

(63) Continuation of application No. 16/872,155, filed on May 11, 2020, now Pat. No. 11,234,727, which is a
(Continued)

(51) Int. Cl.
*A61B 17/3207* (2006.01)
*A61B 17/32* (2006.01)
(Continued)

(52) U.S. Cl.
CPC ............... *A61B 17/320725* (2013.01); *A61B 17/320016* (2013.01); *A61B 18/12* (2013.01);
(Continued)

(58) Field of Classification Search
CPC ...... A61B 17/22031; A61B 17/320016; A61B 17/320725; A61B 17/32075; A61B 18/12;
(Continued)

(56) References Cited

U.S. PATENT DOCUMENTS 3,704,711 A 12/1972 Park
4,794,931 A 1/1989 Yock
(Continued)

FOREIGN PATENT DOCUMENTS

CA 1281381 C 3/1991
CA 2678971 A1 8/2008
(Continued)

OTHER PUBLICATIONS

Corcos, I., "A new autologous venous valve by intimal flap: One Cases report." Note Di Tecnica, Minerva Cardioangiol, 2003, 51, 10 pages.
(Continued)

*Primary Examiner* — Jocelin C Tanner
(74) *Attorney, Agent, or Firm* — Perkins Coie LLP

(57) ABSTRACT

The present technology is directed generally to devices, systems, and methods for capturing and cutting fibrous and trabeculated structures (such as synechiae) in vessel lumens. In one embodiment, the present technology includes an intraluminal tissue modifying system configured to capture the fibrous structures, put the fibrous structures in tension, and controllably cut through the fibrous structures without applying appreciable additional force to the vessel wall. The system may include an expandable capture device and a cutting device.

28 Claims, 21 Drawing Sheets

Related U.S. Application Data continuation of application No. 15/478,143, filed on Apr. 3, 2017, now Pat. No. 10,646,247.

(60) Provisional application No. 62/347,186, filed on Jun. 8, 2016, provisional application No. 62/317,470, filed on Apr. 1, 2016.

(51) Int. Cl.
| | |
|---|---|
| *A61B 18/12* | (2006.01) |
| *A61M 29/02* | (2006.01) |
| *A61B 17/221* | (2006.01) |
| *A61B 17/22* | (2006.01) |
| *A61B 18/00* | (2006.01) |
| *A61B 90/00* | (2016.01) |
| *A61N 7/02* | (2006.01) |
| *A61B 18/14* | (2006.01) |
| *A61M 25/10* | (2013.01) |

(52) U.S. Cl.
CPC ..... *A61B 17/22031* (2013.01); *A61B 18/1492* (2013.01); *A61B 2017/2212* (2013.01); *A61B 2017/22069* (2013.01); *A61B 2017/22097* (2013.01); *A61B 2017/32004* (2013.01); *A61B 2017/320716* (2013.01); *A61B 2018/00404* (2013.01); *A61B 2018/00601* (2013.01); *A61B 2018/00982* (2013.01); *A61B 2018/122* (2013.01); *A61B 2090/3735* (2016.02); *A61B 2090/3782* (2016.02); *A61M 25/104* (2013.01); *A61M 29/02* (2013.01); *A61N 7/022* (2013.01)

(58) Field of Classification Search
CPC ...... A61B 18/1492; A61B 2017/22069; A61B 2017/22097; A61B 2017/2212; A61B 2017/32004; A61B 2017/320716; A61B 2018/00404; A61B 2018/00601; A61B 2018/00982; A61B 2018/122; A61B 2090/3735; A61B 2090/3782; A61M 25/104; A61M 29/02; A61N 7/02
See application file for complete search history.

(56) References Cited

U.S. PATENT DOCUMENTS

| | | | |
|---|---|---|---|
| 4,898,574 A | 2/1990 | Uchiyama et al. | |
| 4,932,962 A | 6/1990 | Yoon et al. | |
| 5,112,339 A | 5/1992 | Zelman et al. | |
| 5,190,046 A | 3/1993 | Shturman et al. | |
| 5,372,601 A | 12/1994 | Lary | |
| 5,443,443 A | 8/1995 | Shiber | |
| 5,464,395 A | 11/1995 | Faxon et al. | |
| 5,601,588 A | 2/1997 | Tonomura et al. | |
| 5,606,975 A | 3/1997 | Liang et al. | |
| 5,695,507 A | 12/1997 | Auth et al. | |
| 5,738,901 A | 4/1998 | Wang et al. | |
| 5,795,322 A | 8/1998 | Boudewijn | |
| 5,810,847 A | 9/1998 | Laufer et al. | |
| 5,836,945 A | 11/1998 | Perkins | |
| 5,882,340 A * | 3/1999 | Yoon .................. | A61B 17/3496 |
| | | | 604/164.12 |
| 5,989,276 A | 11/1999 | Houser et al. | |
| 6,190,353 B1 | 2/2001 | Makower | |
| 6,375,635 B1 | 4/2002 | Moutafis et al. | |
| 6,379,319 B1 | 4/2002 | Garibotto et al. | |
| 6,344,027 B1 | 5/2002 | Goll | |
| 6,458,098 B1 | 10/2002 | Kanesaka | |
| 6,475,226 B1 | 11/2002 | Belef et al. | |
| 6,506,178 B1 | 1/2003 | Schubart et al. | |
| 6,514,217 B1 | 2/2003 | Selmon et al. | |
| 6,524,251 B2 | 2/2003 | Rabiner et al. | |
| 6,676,665 B2 * | 1/2004 | Foley .................. | A61B 17/025 |
| | | | 606/105 |
| 6,685,648 B2 | 2/2004 | Flaherty et al. | |
| 6,692,466 B1 | 2/2004 | Chow | |
| 6,702,744 B2 | 3/2004 | Mandrusov | |
| 6,725,866 B2 | 4/2004 | Johnson et al. | |
| 6,726,677 B1 | 4/2004 | Flaherty et al. | |
| 6,758,836 B2 | 7/2004 | Zawacki | |
| 6,902,576 B2 | 6/2005 | Drasler et al. | |
| 6,913,594 B2 | 7/2005 | Coleman et al. | |
| 7,008,411 B1 | 3/2006 | Mandrusov et al. | |
| 7,056,325 B1 | 6/2006 | Makower et al. | |
| 7,150,738 B2 | 12/2006 | Ray | |
| 7,179,249 B2 | 2/2007 | Steward et al. | |
| 7,273,469 B1 | 9/2007 | Chan et al. | |
| 7,357,795 B2 | 4/2008 | Kaji et al. | |
| 7,517,352 B2 | 4/2009 | Evans | |
| 7,775,968 B2 | 8/2010 | Mathis | |
| 7,780,592 B2 | 8/2010 | Tronnes | |
| 7,918,870 B2 | 4/2011 | Kugler et al. | |
| 7,927,305 B2 | 4/2011 | Yribarren et al. | |
| 7,931,594 B2 | 4/2011 | Hirsh | |
| 7,938,819 B2 | 5/2011 | Kugler et al. | |
| 7,955,346 B2 | 6/2011 | Mauch et al. | |
| 8,025,655 B2 | 9/2011 | Kugler et al. | |
| 8,083,726 B1 | 12/2011 | Wang | |
| 8,083,727 B2 | 12/2011 | Kugler et al. | |
| 8,100,860 B2 | 1/2012 | Von Oepen et al. | |
| 8,114,123 B2 | 2/2012 | Brenzel et al. | |
| 8,177,748 B1 | 5/2012 | Beyerlein | |
| 8,177,802 B2 | 5/2012 | Mauch et al. | |
| 8,267,947 B2 | 9/2012 | Pantages et al. | |
| 8,323,261 B2 | 12/2012 | Kugler | |
| 8,460,316 B2 | 6/2013 | Wilson et al. | |
| 8,636,712 B2 | 1/2014 | Kugler et al. | |
| 8,753,366 B2 | 6/2014 | Makower et al. | |
| 9,320,504 B2 | 4/2016 | Wilson et al. | |
| 9,381,034 B2 | 7/2016 | Kawwei | |
| 9,545,289 B2 | 1/2017 | Wilson et al. | |
| 9,814,538 B2 | 11/2017 | Kugler et al. | |
| 9,827,005 B2 | 11/2017 | Wilson et al. | |
| 9,949,752 B2 | 4/2018 | Wilson et al. | |
| 9,955,990 B2 | 5/2018 | Wilson et al. | |
| 10,105,157 B2 | 10/2018 | Wilson et al. | |
| 10,188,419 B2 | 1/2019 | Wilson et al. | |
| 10,231,613 B2 | 3/2019 | Wilson et al. | |
| 10,292,807 B2 | 5/2019 | Wilson et al. | |
| 10,603,018 B2 | 3/2020 | Wilson et al. | |
| 10,646,247 B2 * | 5/2020 | Wilson .......... | A61B 17/320725 |
| 10,874,413 B2 | 12/2020 | Wilson et al. | |
| 2001/0041899 A1 | 11/2001 | Foster | |
| 2002/0029052 A1 | 3/2002 | Evans et al. | |
| 2002/0072706 A1 | 6/2002 | Hiblar et al. | |
| 2002/0091362 A1 | 7/2002 | Maginot | |
| 2002/0103459 A1 | 8/2002 | Sparks et al. | |
| 2003/0144670 A1 * | 7/2003 | Pavcnik ................ | A61F 2/2436 |
| | | | 606/108 |
| 2004/0167558 A1 | 8/2004 | Igo et al. | |
| 2004/0215339 A1 | 10/2004 | Drasler et al. | |
| 2005/0014995 A1 | 1/2005 | Amundson et al. | |
| 2005/0075665 A1 | 4/2005 | Brenzel et al. | |
| 2005/0165466 A1 | 7/2005 | Morris et al. | |
| 2005/0273159 A1 | 12/2005 | Opie | |
| 2006/0094929 A1 | 5/2006 | Tronnes | |
| 2006/0136045 A1 | 6/2006 | Flagle et al. | |
| 2006/0156875 A1 | 7/2006 | McRury et al. | |
| 2006/0178646 A1 | 8/2006 | Harris et al. | |
| 2006/0184187 A1 | 8/2006 | Surti | |
| 2006/0235449 A1 | 10/2006 | Schubart et al. | |
| 2006/0271090 A1 | 11/2006 | Shaked et al. | |
| 2007/0005093 A1 * | 1/2007 | Cox ..................... | A61B 90/30 |
| | | | 606/198 |
| 2007/0093780 A1 | 4/2007 | Kugler | |
| 2007/0093781 A1 | 4/2007 | Kugler et al. | |
| 2007/0208368 A1 | 9/2007 | Katoh et al. | |
| 2008/0033467 A1 | 2/2008 | Miyamoto et al. | |
| 2008/0103480 A1 | 5/2008 | Bosel et al. | |
| 2008/0228171 A1 | 9/2008 | Kugler et al. | |
| 2008/0228211 A1 | 9/2008 | Gonon | |
| 2008/0243065 A1 | 10/2008 | Rottenberg et al. | |

(56) References Cited

U.S. PATENT DOCUMENTS

| | | |
|---|---|---|
| 2008/0255595 A1* | 10/2008 | Buchbinder ... A61B 17/320725 606/159 |
| 2009/0005793 A1 | 1/2009 | Pantages et al. |
| 2009/0112059 A1 | 4/2009 | Nobis |
| 2009/0149739 A9 | 6/2009 | Maschke |
| 2009/0182192 A1 | 7/2009 | Shiono et al. |
| 2009/0209910 A1 | 8/2009 | Kugler et al. |
| 2009/0254051 A1 | 10/2009 | Von Oepen et al. |
| 2009/0270799 A1 | 10/2009 | Seto et al. |
| 2010/0076476 A1 | 3/2010 | To et al. |
| 2010/0152843 A1 | 6/2010 | Mauch et al. |
| 2010/0241147 A1 | 9/2010 | Maschke |
| 2010/0256599 A1 | 10/2010 | Kassab et al. |
| 2011/0264127 A1 | 10/2011 | Mauch et al. |
| 2011/0264128 A1 | 10/2011 | Mauch et al. |
| 2012/0289987 A1 | 11/2012 | Wilson et al. |
| 2013/0066346 A1 | 3/2013 | Pigott et al. |
| 2013/0103070 A1 | 4/2013 | Kugler et al. |
| 2013/0116715 A1 | 5/2013 | Weber |
| 2013/0172883 A1 | 7/2013 | Lopes et al. |
| 2013/0216114 A1 | 8/2013 | Courtney et al. |
| 2013/0317534 A1* | 11/2013 | Zhou ... A61B 17/3207 606/185 |
| 2015/0057566 A1 | 2/2015 | Vetter et al. |
| 2015/0112188 A1 | 4/2015 | Stigall et al. |
| 2016/0081656 A1 | 3/2016 | Abraham |
| 2018/0214173 A1 | 8/2018 | Wilson et al. |
| 2018/0289441 A1 | 10/2018 | Wilson et al. |
| 2018/0333166 A1 | 11/2018 | Wilson et al. |
| 2018/0361118 A1 | 12/2018 | Cully et al. |
| 2019/0314620 A1 | 10/2019 | Chang et al. |
| 2020/0275975 A1 | 9/2020 | Chen |
| 2020/0337726 A1 | 10/2020 | Wilson et al. |

FOREIGN PATENT DOCUMENTS

| | | |
|---|---|---|
| CN | 1907243 A | 2/2007 |
| CN | 1957861 A | 5/2007 |
| JP | 2002514111 A | 5/2002 |
| JP | 2003033357 A | 2/2003 |
| JP | 2003267160 A | 9/2003 |
| JP | 2009165822 A | 7/2009 |
| JP | 2009183516 A | 8/2009 |
| RU | 2108751 C1 | 4/1998 |
| RU | 2160057 C2 | 10/2000 |
| WO | 1999000059 A1 | 1/1999 |
| WO | 2008063621 A2 | 5/2008 |
| WO | 2010074853 A1 | 7/2010 |
| WO | 2011106735 A1 | 9/2011 |
| WO | 2012030587 A1 | 3/2012 |
| WO | 2012145444 A2 | 10/2012 |
| WO | 2013119849 A1 | 8/2013 |
| WO | 2013159066 A1 | 10/2013 |
| WO | 2014110460 A1 | 7/2014 |
| WO | 2015077515 A1 | 5/2015 |
| WO | 2015148581 A1 | 10/2015 |
| WO | 2016025733 A1 | 2/2016 |
| WO | 2017210656 A1 | 12/2017 |

OTHER PUBLICATIONS

Lugli, M., et al., Neovalve construction in the deep venous incompetence. J. Vasc. Surg., Jan. 2009, 49(1), 156-62.

Maleti, O., "Neovalve construction in postthrombotic syndrome," J. Vasc. Surg., vol. 34, No. 4, 6 pages.

International Search Report and Written Opinion dated Jun. 15, 2016, International Application No. PCT/US2015/066205, 18 pages.

Foreign Office Action with English Translation dated Sep. 2, 2019 for JP Patent Application No. 2017-533328; 13 pages.

Foreign Office Action with English Translation dated Jun. 15, 2021 for JP Patent Application No. 2020-114030, 9 pages.

Foreign Office Action dated Sep. 10, 2019 for EP Patent Application No. 15817748.5; 6 pages.

Foreign Office Action dated Jul. 20, 2021 for EP Patent Application No. 15817748.5, 5 pages.

* cited by examiner

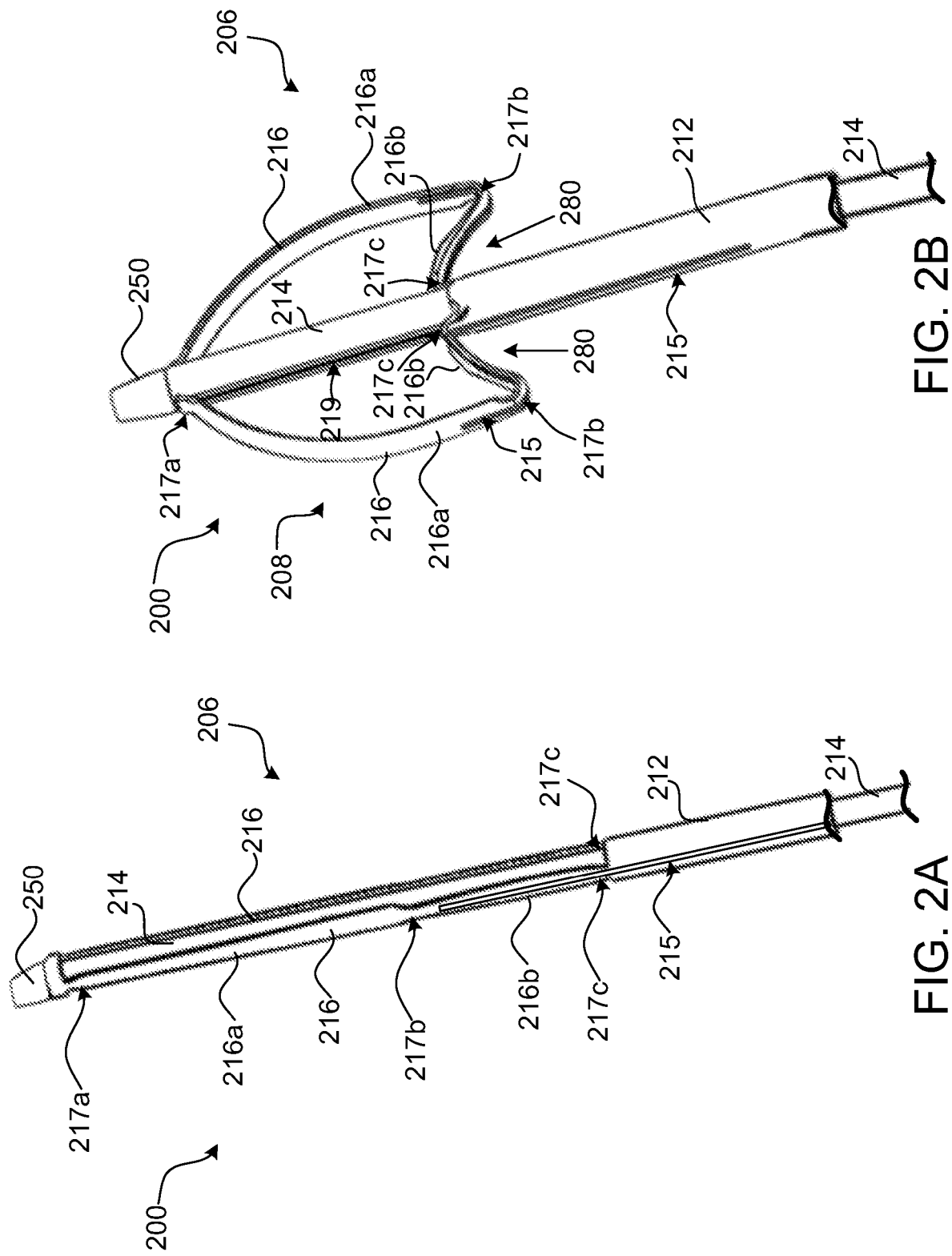

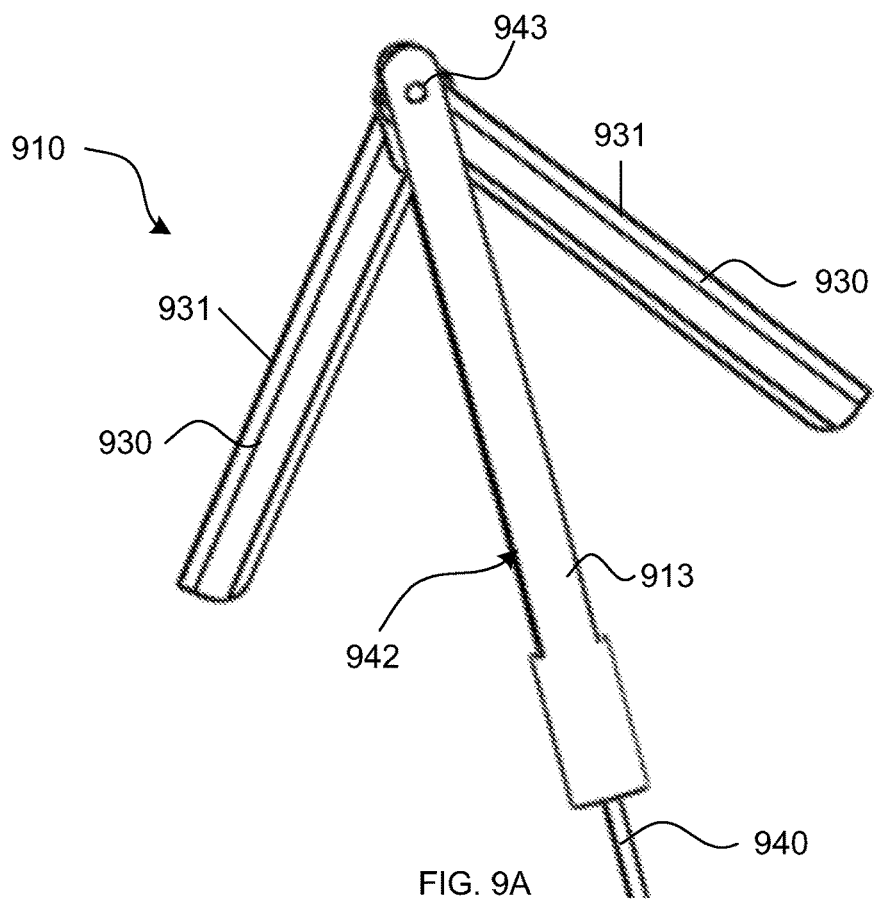
FIG. 9A
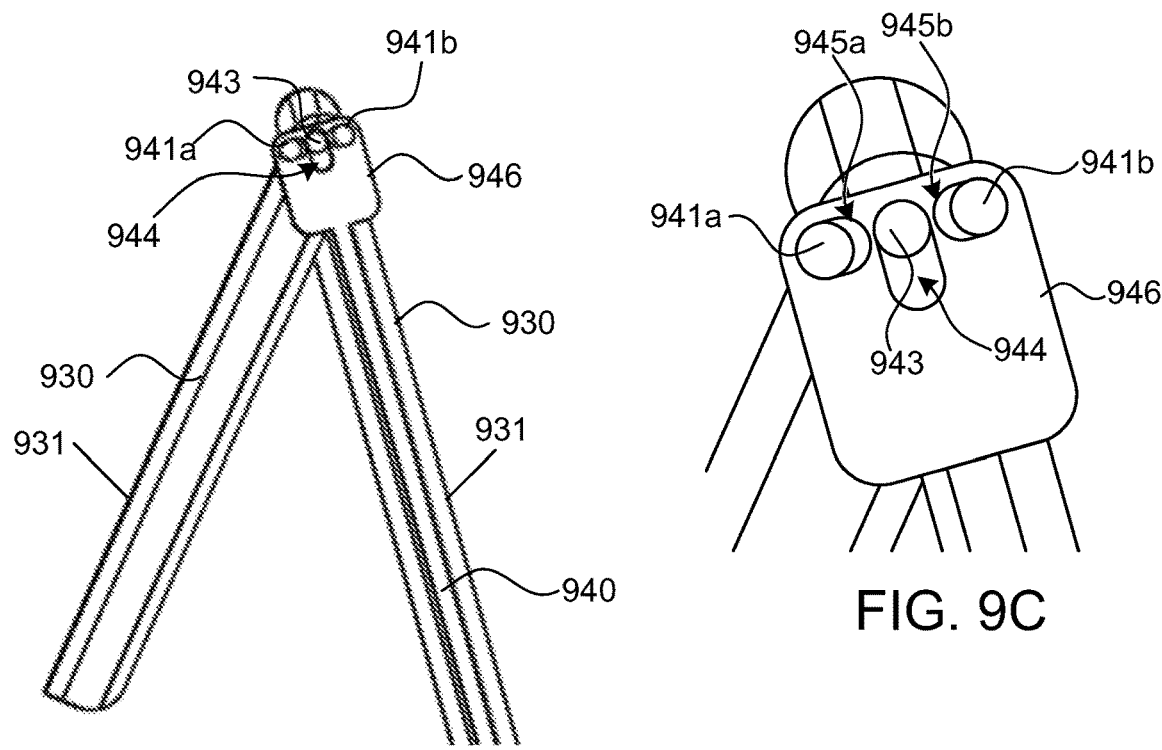
FIG. 9B
FIG. 9C

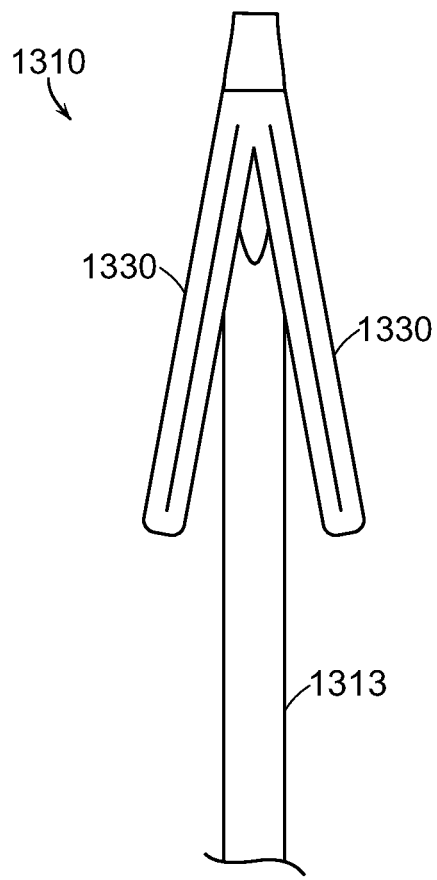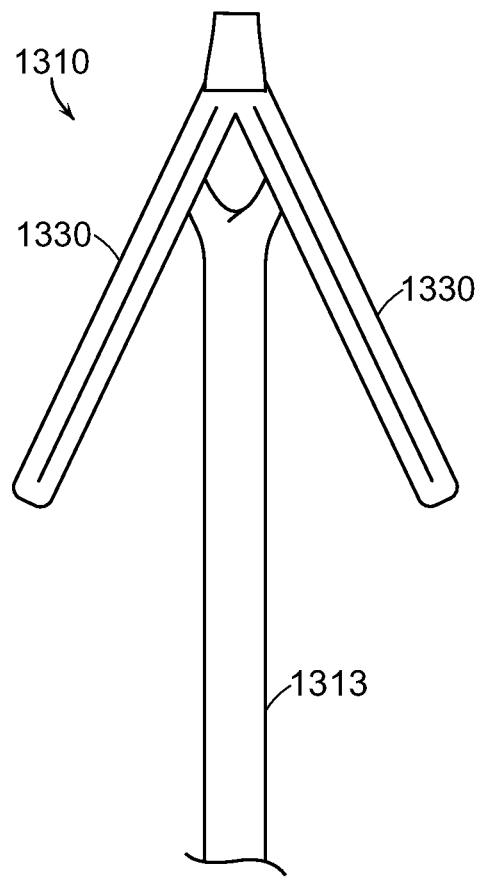
FIG. 13A
FIG. 13B

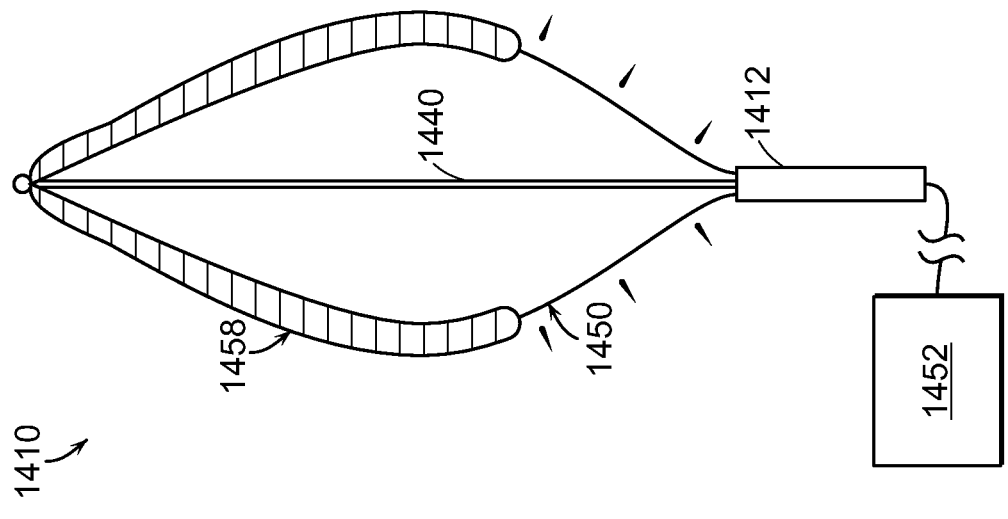
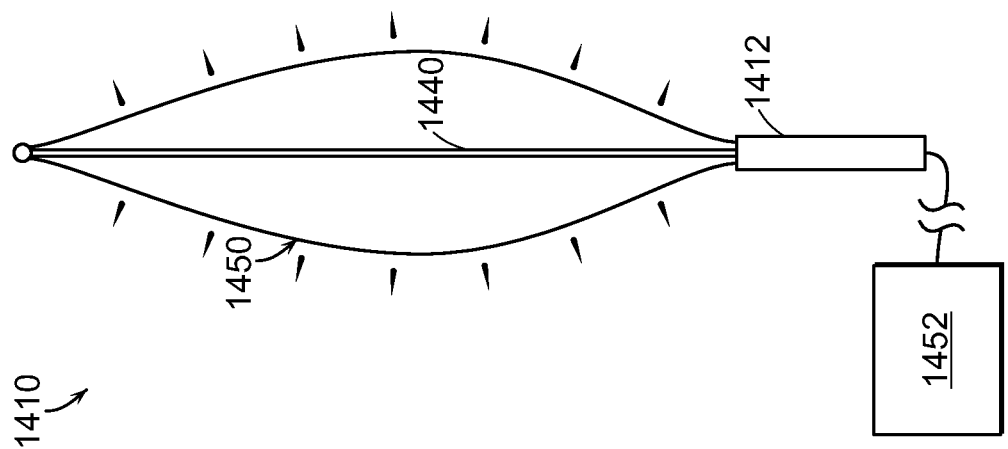
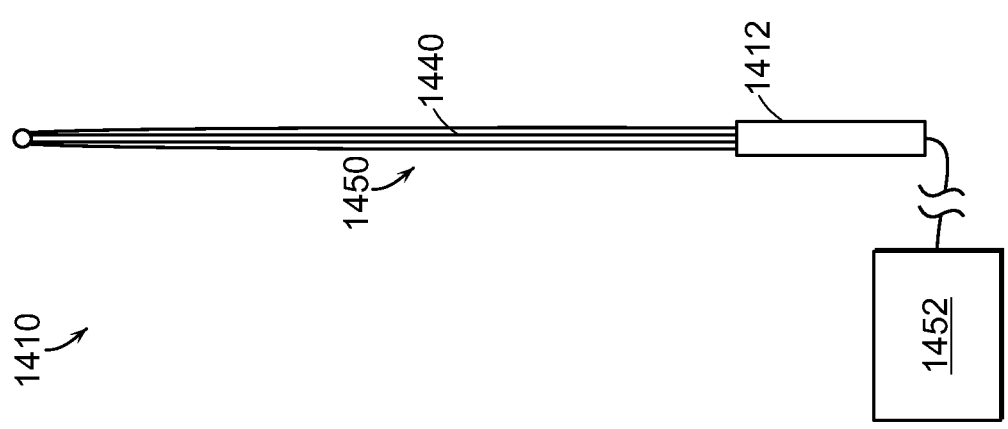

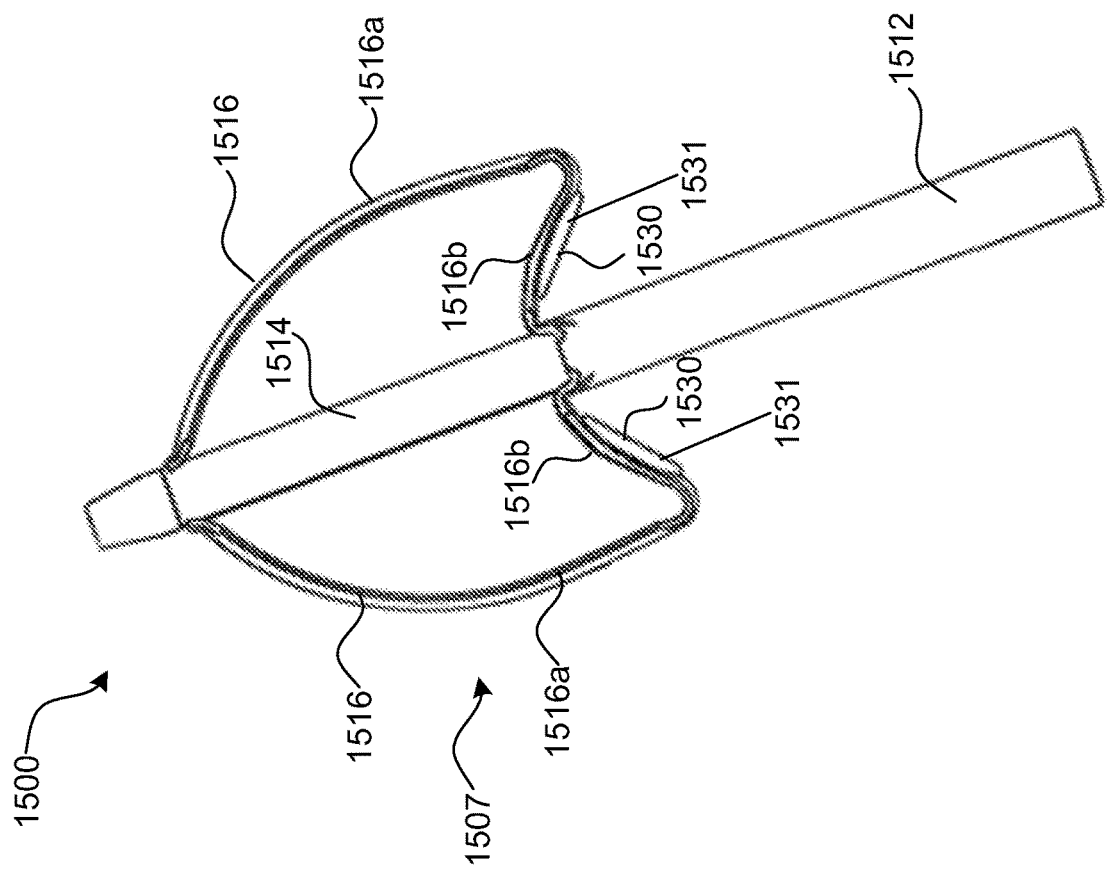
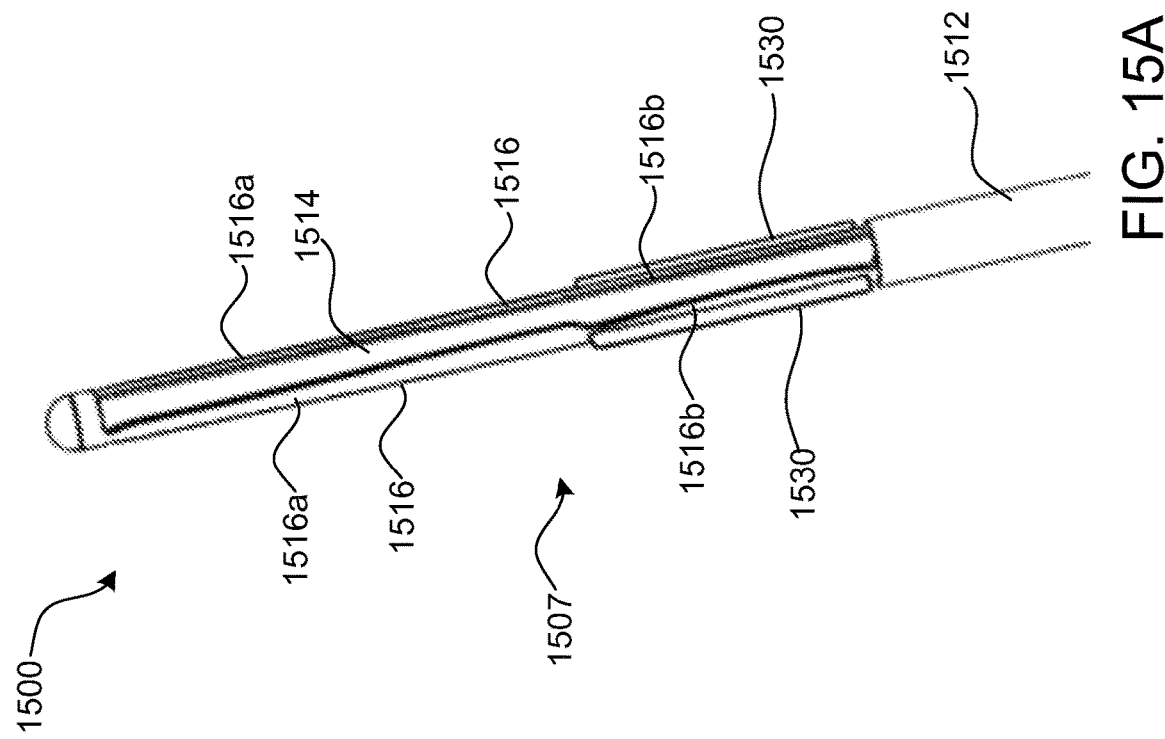
FIG. 15B
FIG. 15A

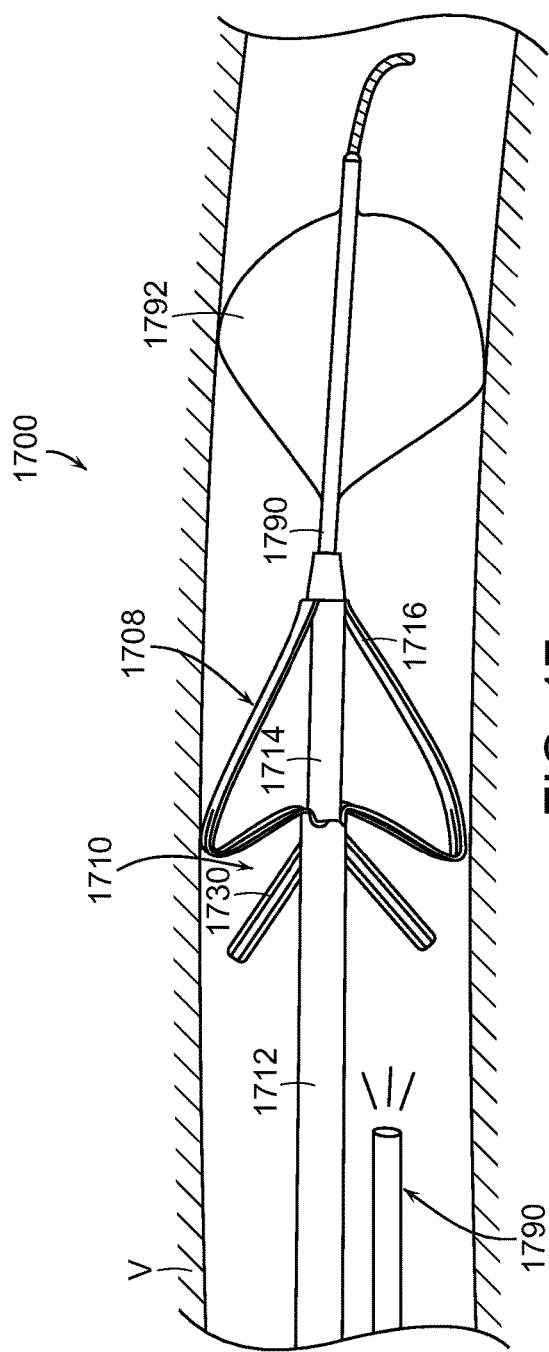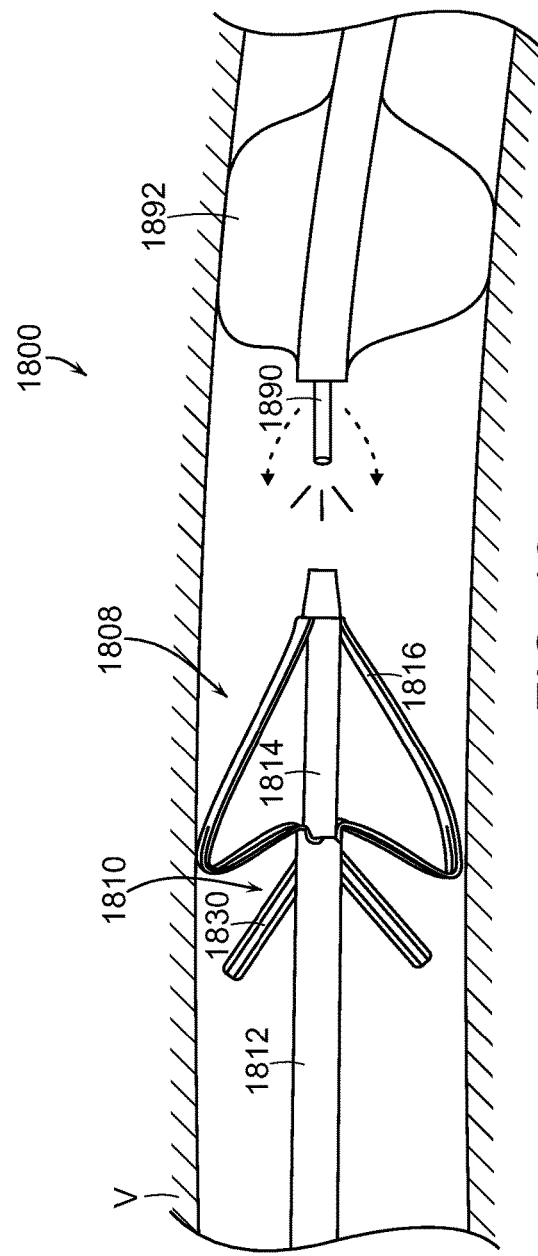

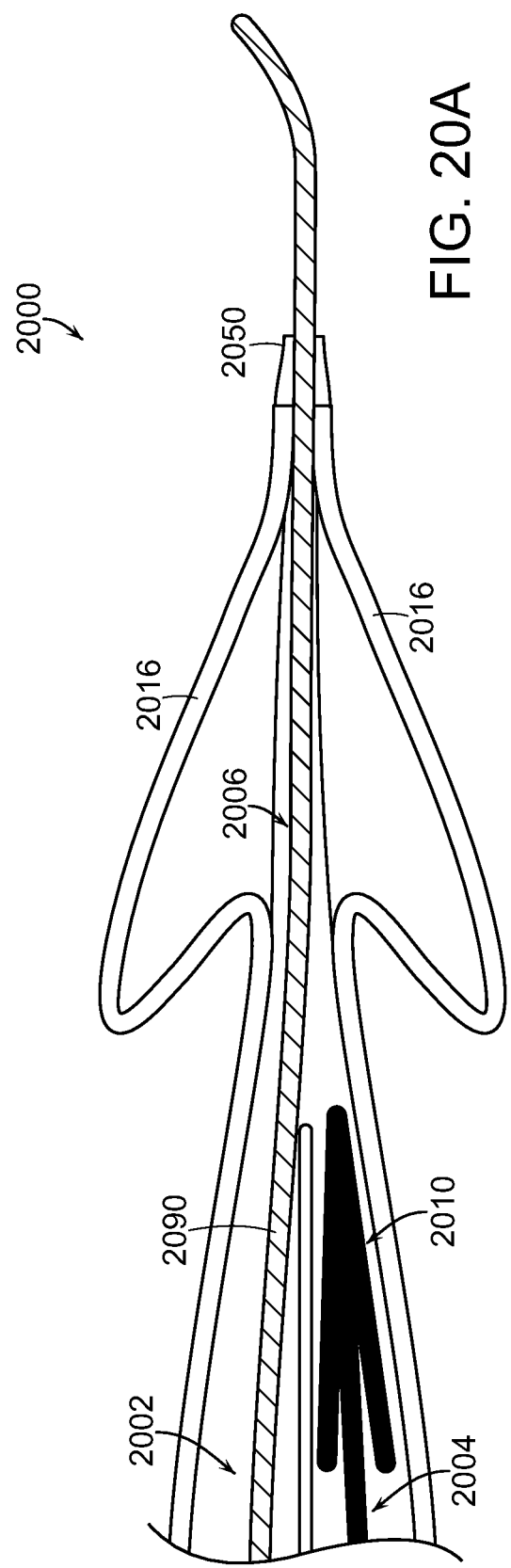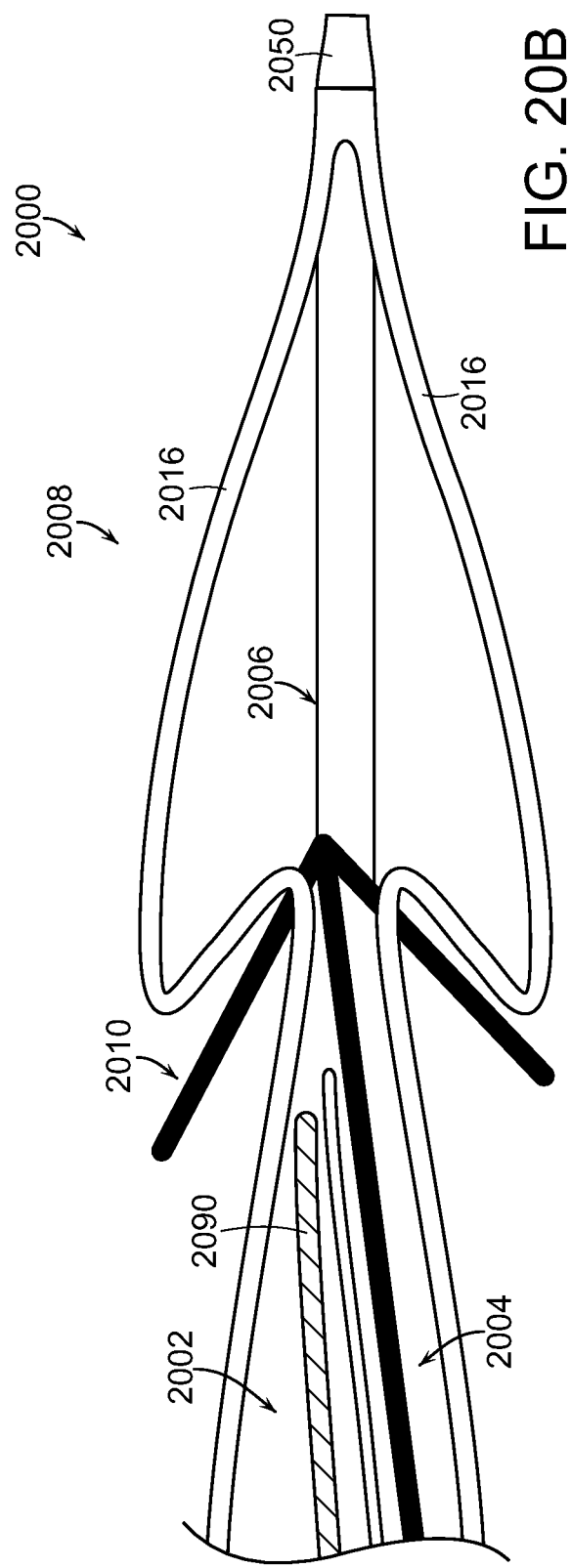

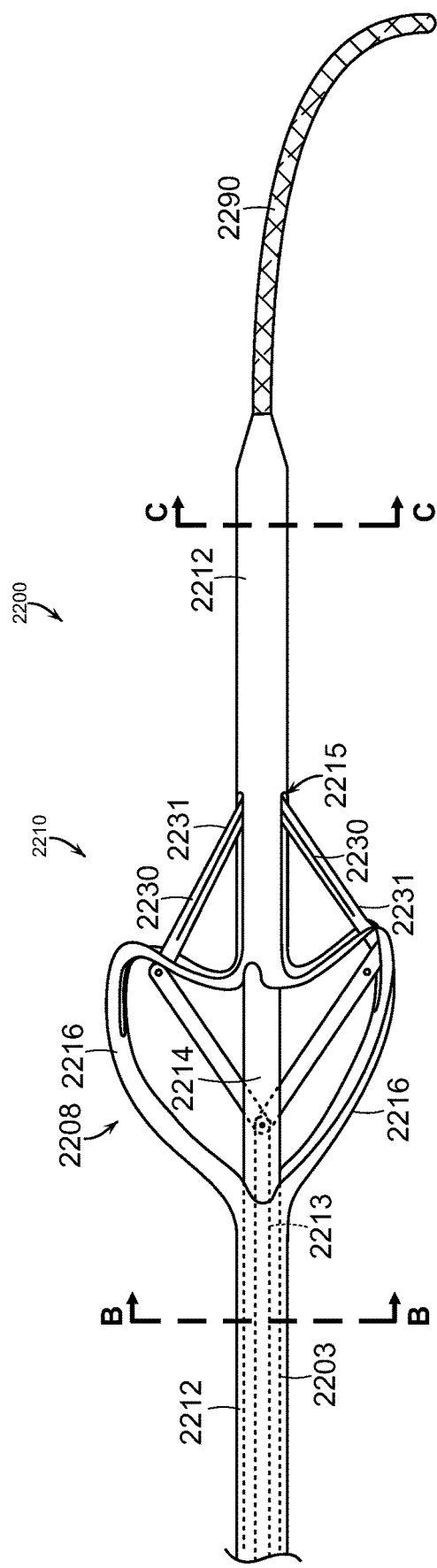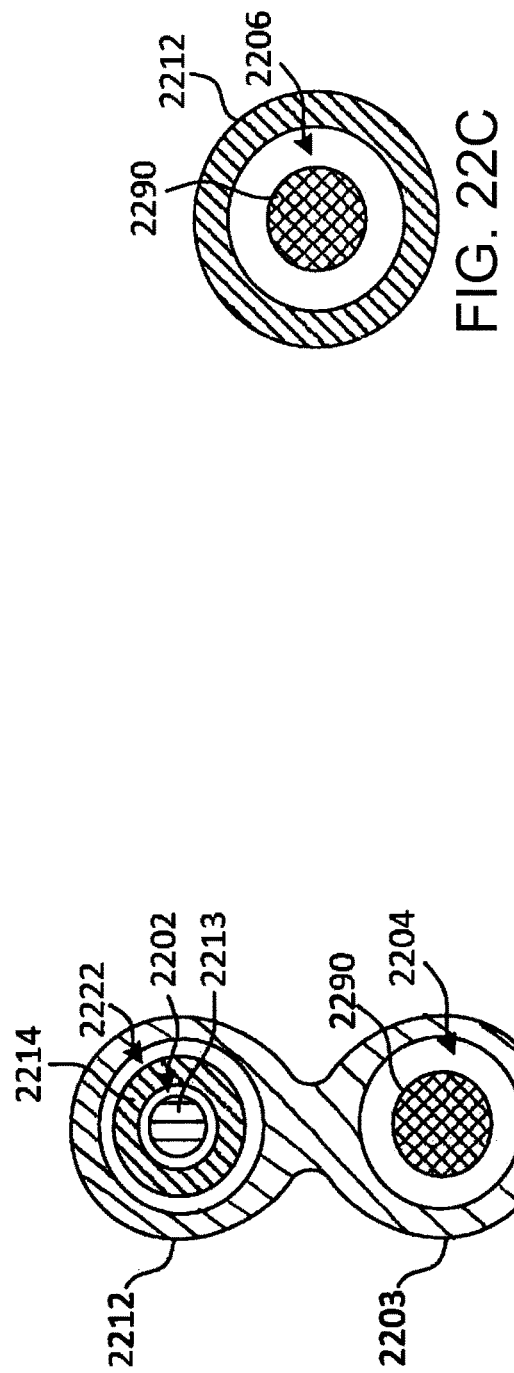
FIG. 22A
FIG. 22B
FIG. 22C

INTRALUMINAL TISSUE MODIFYING SYSTEMS AND ASSOCIATED DEVICES AND METHODS

CROSS-REFERENCE TO RELATED APPLICATION(S)

This application is a continuation of U.S. patent application Ser. No. 16/872,155, filed May 11, 2020, now pending, which is a continuation of U.S. patent application Ser. No. 15/478,143, filed Apr. 3, 2017, now U.S. Pat. No. 10,646,247, which claims the benefit of U.S. Provisional Patent Application No. 62/317,470 filed on Apr. 1, 2016, entitled INTRALUMINAL TISSUE MODIFYING SYSTEMS AND ASSOCIATED DEVICES AND METHODS, and claims the benefit of U.S. Provisional Patent Application No. 62/347,186 filed on Jun. 8, 2016, entitled INTRALUMINAL TISSUE MODIFYING SYSTEMS AND ASSOCIATED DEVICES AND METHODS, all of which are incorporated herein by reference in their entireties.

TECHNICAL FIELD

The present technology is directed generally to intraluminal tissue modifying systems and associated devices and methods.

BACKGROUND

There exists a disease condition in the leg veins called venous synechiae or septae, also called trabeculated or fenestrated veins. All of the foregoing terms refer to flow-obstructing structures present in human veins which are thought to be residual intraluminal scar tissue resulting from long-term presence of fibrotic thrombus. After thrombolysis, either through natural lysis or treatment via thrombolytics or thrombectomy, fibrous structures often remain. This partial obstruction of flow leads to clinical conditions such as hypertension, edema, chronic pain, and non-healing ulcers. The condition is also a risk for further thrombosis, and can also prevent or interfere with interventions such as balloon angioplasty or stenting.

Venous synechiae restrict blood flow via two mechanisms: (1) reduction of the effective luminal cross-sectional area due to their physical presence, and (2) reduction of the overall venous luminal diameter caused by stored tension in the synechiae that pulls the vessel walls inward. Puggioni et al carried out endophlebectomies, or removal of venous synechiae, on 13 patients in an open surgical fashion. In this experience, Puggioni describes the second, more subtle obstructive impact of venous synechiae: "After removal of the synechiae, an increase in luminal diameter is observed as a result of the release of constricting bands, and this contributes to improved vessel compliance." Puggioni et al. Surgical disobliteration of postthrombotic deep veins—endophlebectomy—is feasible. J Vasc Surg 2004; 39:1048-52.

While complete removal of venous synechiae may be ideal for maximizing restoration of flow to a venous lumen, there is a clinical benefit to relieving the tension imposed on the vessel wall by cutting the synechiae. Cutting the synechiae also enables intraluminal delivery of a balloon catheter or stent delivery system which can then be deployed to expand the vessel (via dilation or stenting).

Individual synechiae are often tough and fibrous in nature, and can also be quite dense in the vessel lumen. Current methods for treating or otherwise reducing the physiological impact of the synechiae include the use of cutting balloons, balloon angioplasty, or stenting to cut through the fibrous synechiae structures. However, such methods have proven to have limited efficacy on restoring flow due to the toughness and/or density of the obstructions. Direct surgical excision of the synechiae have also been attempted but open vascular surgical procedures can themselves lead to post-surgical complications such as hematoma, infection, thrombosis, or restenosis. Furthermore, a direct surgical approach cannot easily treat long lengths of veins or multiple sites in one patient without causing increased trauma to the patient.

One existing approach for cutting intraluminal fibers involves a device with a grasping component and a tubular member with internal cutting devices. In this approach, the grasper pulls fibers into the tubular member where they are severed on contact with the cutting devices. However, the design of such a device has limited ability to cut across the entire diameter of a vessel, or to cut through the bulk of fibrous material often seen in the veins. Other cutting catheter technology exists, such as cutting balloons, atherectomy devices, chronic total occlusion catheter, or embolectomy catheters. However, none of these devices were designed for cutting fibrous and bulky intravascular structures, and are therefore limited in their ability to treat these conditions. Devices such as valvulotomes are designed to remove existing valves from veins, for example in procedures utilizing veins in connection with in situ bypass graft placement or treating AV fistulas. However, vein valves are relatively thin structures and valvulotome devices are not designed to cut particularly tough tissue. As such, valvutome devices would be unsuitable for cutting tissue structures such as venous synechiae. Also, these technologies require the user to pull the device past the tissue in order to cut, thus applying a shear force on the vessel wall and surrounding tissue. If there is any resistance to cutting, the applied force may result in considerable pain to the patient. Even in cases requiring minimal force, the act of cutting will result in losing access across the treatment site and requiring re-accessing the site if the cuts were unsuccessful or inadequate on the initial pass.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 2A is an isometric view of a distal portion of another embodiment of an intraluminal tissue modifying system configured in accordance with the present technology, shown in a low-profile state.

FIGS. 2B-2D are isometric views of the distal portion of the intraluminal tissue modifying system shown in FIG. 2A, shown in several different deployed states.

FIG. 9A is a front view of a distal portion of a cutting device configured in accordance with the present technology, shown in a deployed state.

FIG. 9B is a front, isolated view of a portion of the cutting device shown in FIG. 9A.

FIG. 9C is an enlarged view of a portion of FIG. 9B.

FIGS. 13A and 13B are isometric views of a distal portion of another embodiment of a cutting device configured in accordance with the present technology, shown in a low-profile state and a deployed state, respectively.

FIGS. 14A-14C show several embodiments of cutting devices configured in accordance with the present technology.

FIGS. 15A and 15B are isometric views of a distal portion of an intraluminal tissue modifying system configured in accordance with the present technology, shown in a low-profile state and a deployed state, respectively.

FIGS. 17 and 18 show further embodiments intraluminal modifying systems configured in accordance with the present technology.

FIGS. 20A and 20B show another embodiment of an intraluminal tissue modifying system configured in accordance with the present technology, shown during different stages of deployment.

FIG. 22A shows another embodiment of an intraluminal tissue modifying system configured in accordance with the present technology.

FIG. 22B is a cross-sectional end view taken along line B-B in FIG. 22A.

FIG. 22C is a cross-sectional end view taken along line C-C in FIG. 22A.

DETAILED DESCRIPTION

The present technology is directed generally to devices, systems, and methods for capturing and cutting fibrous and trabeculated structures (such as synechiae) in vessel lumens. In one embodiment, the present technology includes an intraluminal tissue modifying system configured to capture the fibrous structures, put the fibrous structures in tension, and controllably cut through the fibrous structures without applying appreciable additional force to the vessel wall. As described in greater detail below, the system includes an expandable capture device and a cutting device. The capture device and cutting device can be separate components or can be integrated into the same component. In some embodiments, the system can also be configured for use with one or more visualization devices and/or therapeutic devices such as balloon catheters, stents, and the like.

Figure 1:
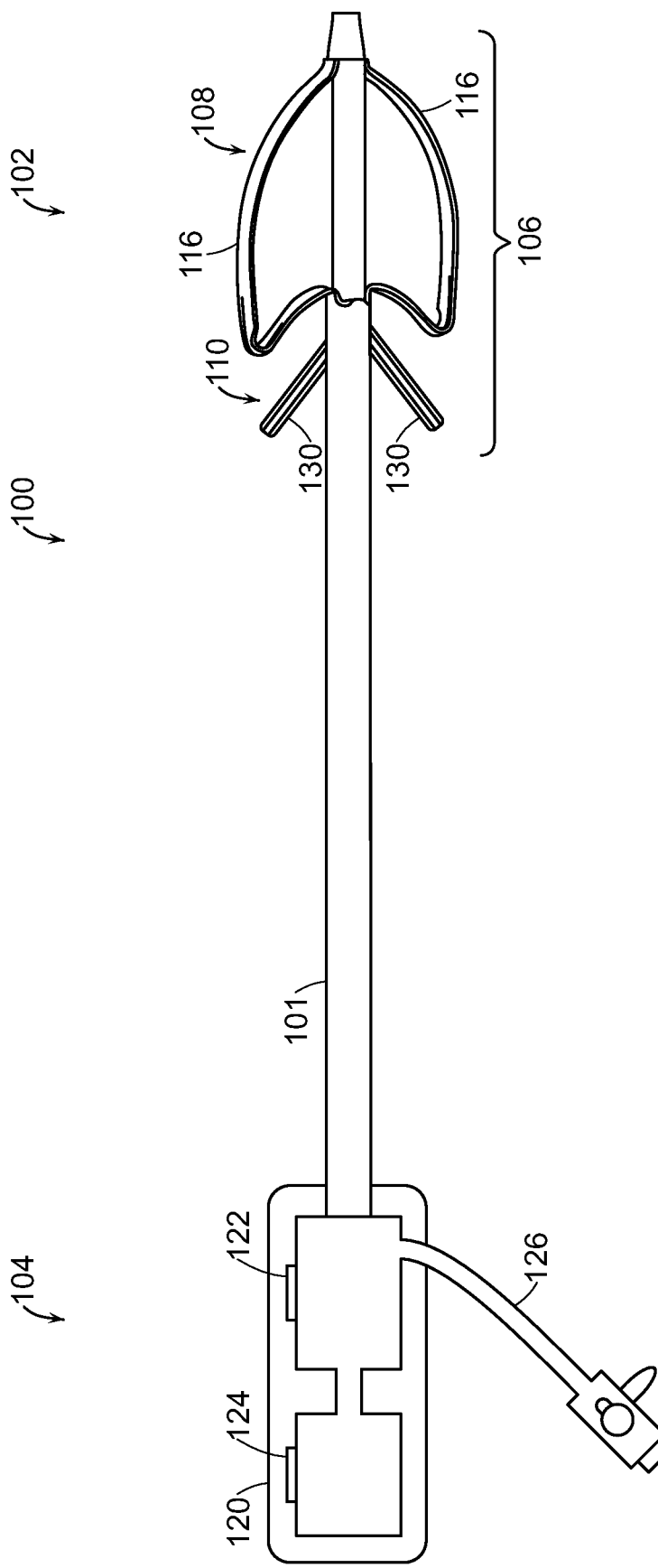
FIG. 1 is a partially schematic overview of an intraluminal tissue modifying system configured in accordance with the present technology, shown in a deployed state.

FIG. 1 is a partially schematic overview of one embodiment of an intraluminal tissue modifying system 100 (also referred to herein as "the system 100") configured in accordance with the present technology, shown in a deployed state. As shown in FIG. 1, the system 100 has an elongated shaft 101, a distal portion 102 configured to be positioned at a treatment site within a blood vessel (e.g., a vein), and a proximal portion 104 configured to be positioned extracorporeally during the procedure. The system 100 includes a handle 120 (shown schematically) at the proximal portion 104. The distal portion 102 of the system 100 includes a tissue modifying region 106. The tissue modifying region 106 is transformable between a low-profile state (not shown) (e.g., for delivery through an introducer sheath or other delivery device into a vessel lumen) and an expanded or deployed state (shown in FIG. 1). As shown in FIG. 1, the tissue modifying region 106 includes a capture device 108 and a cutting device 110. The capture device 108 can include one or more capture members 116 that, in the deployed state, extend outwardly away from a central longitudinal axis of the elongated shaft 101 to engage fibrous structures at the treatment site. The cutting device 110 can include one or more blades 130 that, in the deployed state, extend outwardly away from the central longitudinal axis of the elongated shaft 101 to cut tissue at the treatment site.

Referring still to the embodiment shown in FIG. 1, the handle 120 includes a first actuator 122 mechanically (e.g., via a push rod, push tube, and/or pull-wire extending through the shaft 101) and/or electrically (e.g., via one or more wires extending through the shaft 101) coupled to the capture device 108 and a second actuator 124 mechanically (e.g., via a push rod, push tube, and/or pull-wire extending through the shaft 101) and/or electrically coupled to the cutting device 110. Activation of the first actuator 122 deploys (e.g., expands) the capture members 116 of the capture device 108, and activation of the second actuator 124 deploys (e.g., expands) the blades 130 of the cutting device 110. In some embodiments, the handle 120 also includes a third actuator (not shown in FIG. 1) configured to move the cutting device 110 axially with respect to the capture device 108 (or vice versa). In a particular embodiment, the handle 120 may also include a connection to a flush line 126. The flush line can be fluidly connected to the distal portion 102 of the system 100 (e.g., via a lumen of the shaft 101).

In some methods of use, the system 100 can be introduced into the venous system from a proximal site (e.g., the femoral vein) and advanced in a retrograde direction (against normal blood flow) to a treatment site in a leg vein. The system 100 can be also be introduced into the venous system from a distal site (e.g., a popliteal or more distal vein) and advanced in an antegrade direction (same direction as blood flow) towards the target treatment site.

Figure 2D:
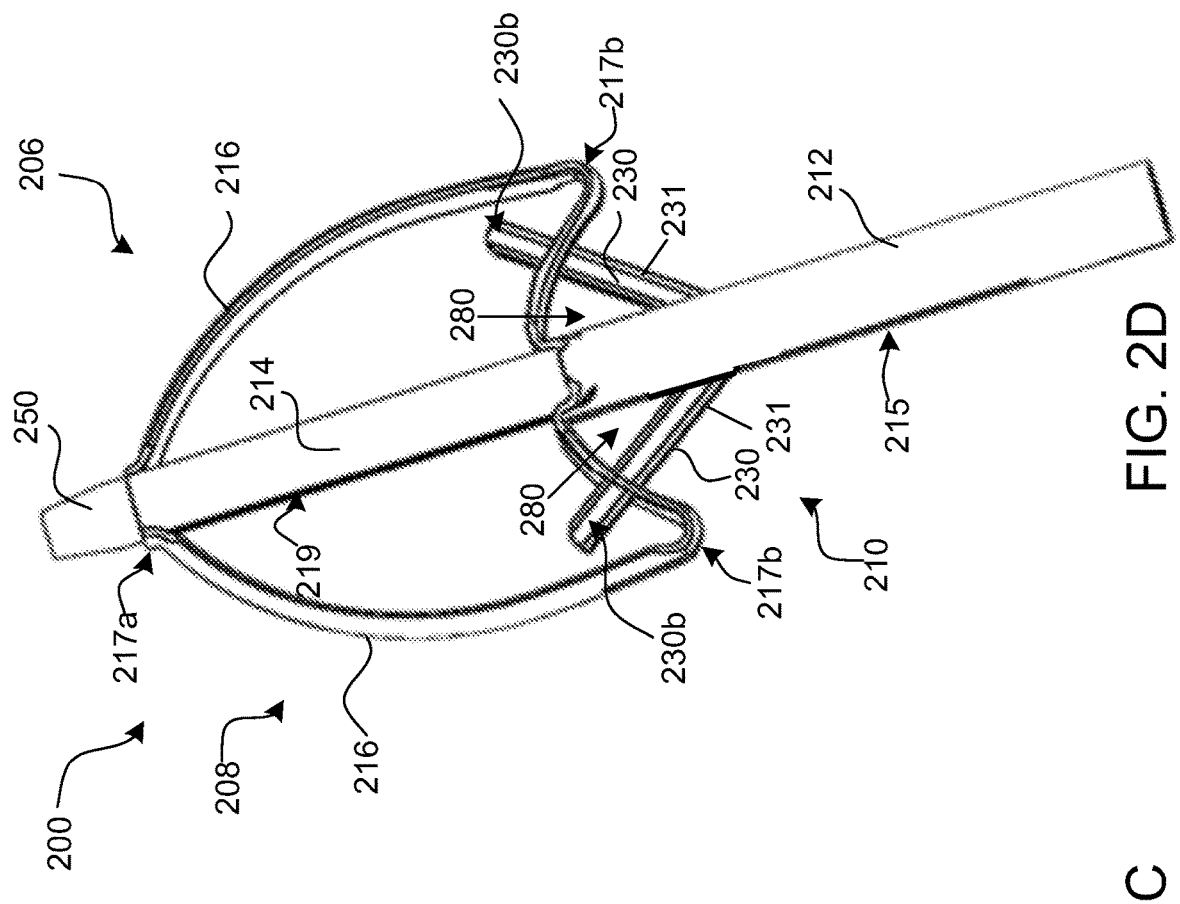
Figure 2C:
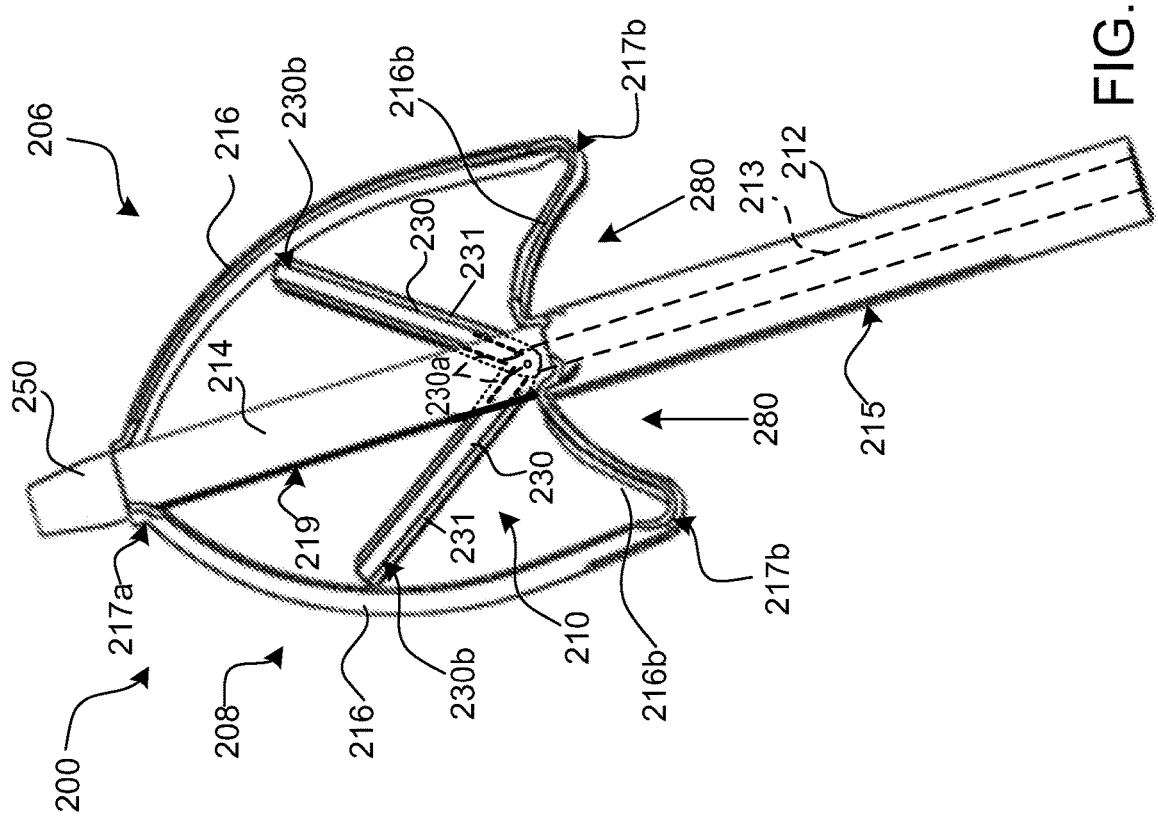

FIGS. 2A-2D are isometric views of a distal portion of an intraluminal tissue modifying system 200 ("or modifying system 200"), shown in different states of deployment. Referring to FIGS. 2A-2D together, the system 200 includes a capture device 208 (only a distal portion shown) and a cutting device 210 (only a distal portion shown in FIGS. 2C and 2D) slidably received through at least a portion of the capture device 208. In FIG. 2A, the system 200 is shown in a low-profile or delivery state in which both the capture device 208 and the cutting device 210 are in a low-profile or delivery state. FIG. 2B shows a distal portion of the capture device 208 in a deployed state while the cutting device 210 (not visible) remains in a low-profile state (and/or has not yet been advanced to the distal portion of the capture device 208). FIGS. 2C and 2D are isometric views of the modifying system 200 with the capture device 208 in a deployed state and the cutting device 210 in first and second deployed states, respectively. As used to describe the any of the intraluminal tissue modifying systems herein, "deployed" or "expanded" state refers to the tissue modifying system when one or both of the corresponding capture device and the corresponding cutting device are in the expanded or deployed states.

Referring again to FIGS. 2A-2D together, the distal portions of the capture device 208 and the cutting device 210 together comprise a tissue modifying region 206 of the system 200. The tissue modifying region 206 is transformable between a low-profile state (FIG. 2A) for delivery through an introducer sheath (or other delivery device) to a treatment site within a vessel lumen, and an expanded or deployed state (any of FIGS. 2B-2D) for engaging and cutting tissue at the treatment site, as described in greater detail below.

The capture device 208 can include an outer shaft 212 and an inner shaft 214 disposed within a lumen of the outer shaft 212. The capture device 208 and/or the inner shaft 214 may have an atraumatic distal end region 250. As shown in FIGS. 2A-2D, one or more regions of the outer shaft 212 have been removed along the distal portion to form expandable capture members 216. A distal end region of the outer shaft 212 can be fixed to the distal end region 250 of the inner shaft 214. As such, proximal movement of the inner shaft 214 with respect to the outer shaft 212 pulls the distal portions of the capture members 216 proximally and forces the capture members 216 to bend outwardly away from the longitudinal axis of the shaft 212, as shown in FIGS. 2C-2D.

The capture members 216 can include one or more segments (referred to collectively as segments 201; labeled individually as first and second segments 216a, 216b) and one or more joints 217 (referred to individually as first-third joints 217a-c). The joints 217 can be positioned along the capture members 216 between successive segments 201 and/or at the portions of the capture members 216 that meet the shaft 212 (e.g., the proximal and distal end portions of the capture members 216). The joints 217 can be portions of the capture members 216 and/or shaft 212 configured to preferentially flex or bend relative to the segments 201 and/or the shaft 212. In some embodiments, one or more of the joints 217 can be formed by opposing recesses at a desired location along the capture member 216 (e.g., a living hinge), and in other embodiments one or more of the joints 217 can be one or more small pins, elastic polymeric elements, mechanical hinges and/or other devices that enable one segment 201 to pivot or bend relative to another.

In the embodiment shown in FIGS. 2A-2D, each of the capture members 216 includes a distal joint 217a at its distal end portion, a proximal joint 217c (only labeled in FIGS. 2A and 2B) at its proximal end portion, and an intermediate joint 217b positioned along the length of the respective capture member 216 between the distal and proximal joints 217a, 217c. In response to longitudinal stresses caused by proximal movement of the intermediate shaft 214, the capture members 216 deform into a predetermined shape biased by the configuration and/or relative positions of the joints 217. For example, in the illustrated embodiment, each of the capture members 216, when deployed, include a generally curved distal segment 216a and a generally curved, concave proximal segment 216b. The individual proximal segments 216b extend outwardly from the shaft 212 in a proximal direction, thereby forming a capture region 280 between the respective proximal segment 216b and the outer shaft 212 and/or another portion of the proximal segment 216b). In use, the capture members 216 and/or the proximal segments 216b hook or capture targeted tissue within the capture region 280 for subsequent cutting and/or other modification.

The cutting device 210 can be slidably received within a lumen of the inner shaft 214 of the capture device 208. The cutting device 210 can include an elongated shaft 213 (shown in dashed lines in FIG. 2C) and one or more cutting elements, such as blades 230, rotatably coupled to a distal portion of the shaft 213. In the embodiment shown in FIGS. 2A-2D, each of the blades 230 has a first end portion 230a (shown in dashed lines in FIG. 2C), a second end portion 230b opposite the first end portion 230a, and a sharpened edge 231 that faces proximally when the cutting device 210 is in the deployed state. The first end portions 230a are rotatably coupled to a distal portion of the inner member 213 and, when the cutting device 210 is in a deployed state (such as the deployed states shown in FIGS. 2C and 2D), the first end portions 230a are (1) positioned proximal of the second end portions 230b, and (2) positioned closer to a central longitudinal axis of the inner member 213 than the second end portions 230b. In the deployed state, the blades 230 extend outwardly away from the central longitudinal axis of the shaft 213 through slots 215 in the outer shaft 212 and corresponding slots 211 in the intermediate shaft 214 to cut tissue at the treatment site. In use, the cutting device 210 can be deployed or expanded within an interior region enclosed by the capture members 216 of the capture device 208 and pulled proximally to cut the tissue. As the sharpened edge 231 cuts the tissue, the blades 230 provide additional tension on the tissue.

In one method of using the system 200, the tissue modifying region 206, in its low-profile delivery state, is positioned within a blood vessel lumen at a treatment site, such as at or near one or more intraluminal structures such as synechiae. The inner shaft 214 can then be pulled proximally relative to the outer shaft 212 to deploy the capture members 216 of capture device 208 (or the outer shaft 212 can be moved distally relative to the inner shaft 214). Via deployment of the capture device 208 and/or subsequent proximal axial movement of the system 200, the capture members 216 capture one or more intraluminal structures (such as synechiae) for cutting.

Before, during, and/or after deployment of the capture members 216, the cutting device 210 can be deployed such that the blades 230 extend outwardly away from a central longitudinal axis of the outer shaft 212 (and through the slot 215 in the outer shaft and the slot 219 in the intermediate shaft 214) at an axial location that is distal to the proximal joint 217c of the capture members 216 in preparation for cutting. As shown in FIGS. 2C and 2D, the cutting device 210 and/or the blades 230 can be pulled proximally towards the capture members 216 to cut the tissue which has been captured by the capture members 216. The slots 215 along the capture device 208 and outer shaft 212 and the slots 219 along the intermediate shaft 214 allow the cutting device 210 to move proximally of interior region 280 enclosed by the capture members 216. In this embodiment, the captured tissue can be held in tension while the tissue is being cut by the blades 230 by pulling the capture device 208 proximally. The capture members 216 themselves may also provide tension in an outward direction.

Figures 3A, 3B:
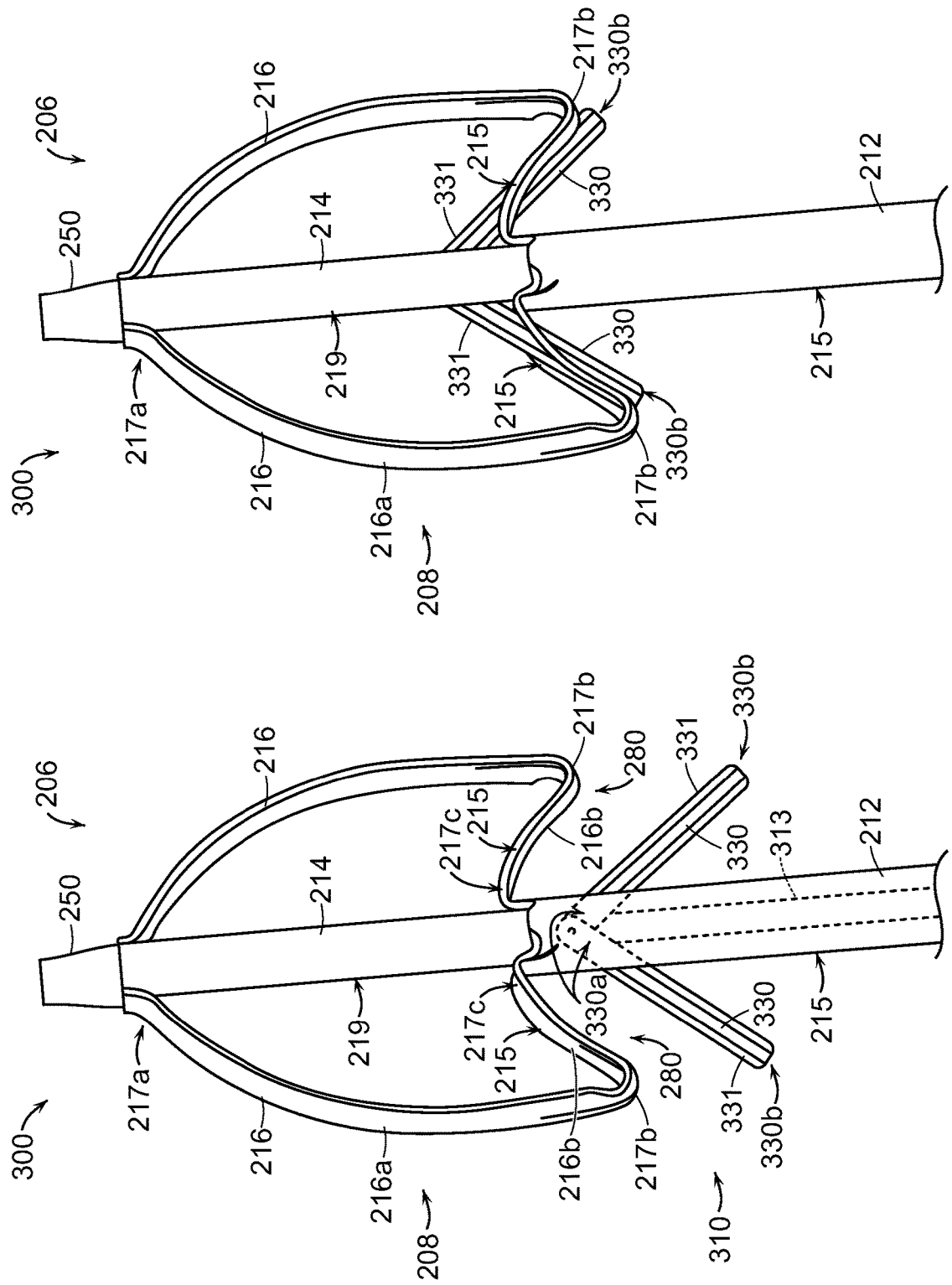
FIGS. 3A and 3B are isometric views of a distal portion of an intraluminal tissue modifying system configured in accordance with the present technology, shown in a first deployed state and a second deployed state, respectively.

FIGS. 3A and 3B are isometric views of a distal portion of an intraluminal tissue modifying system 300 ("or modifying system 300") configured in accordance with another embodiment of the present technology, shown in a first and second deployed state. The components of the modifying system 300 can be generally similar to the components of the modifying system 200 shown in FIGS. 2A-2D except each of the blades 330 of the cutting device 310 of FIGS. 3A and 3B has a sharpened edge 331 that faces distally when the cutting device 310 is in the deployed state (such as the first and second deployed states). As such, to cut tissue captured within the capture region 280 of the capture device 208, the cutting device 310 is pushed distally, as shown in FIG. 3B. When the cutting device 310 is in a deployed state, the first end portions 330a (shown in dashed lines in FIG. 3A) are (1) positioned distal of the second end portions 330b, and (2) positioned closer to a central longitudinal axis of the inner member 313 (only shown in FIG. 3A) than the second end portions 330b. In use, the cutting device 310 can be deployed or expanded proximal of the arms 216 of the capture device 208 and pushed distally through the slots 215 in the capture members 216 to cut the tissue in the capture region 280. As the sharpened edge 331 cuts the tissue, the blades 330 provide additional tension on the tissue.

Figure 4:
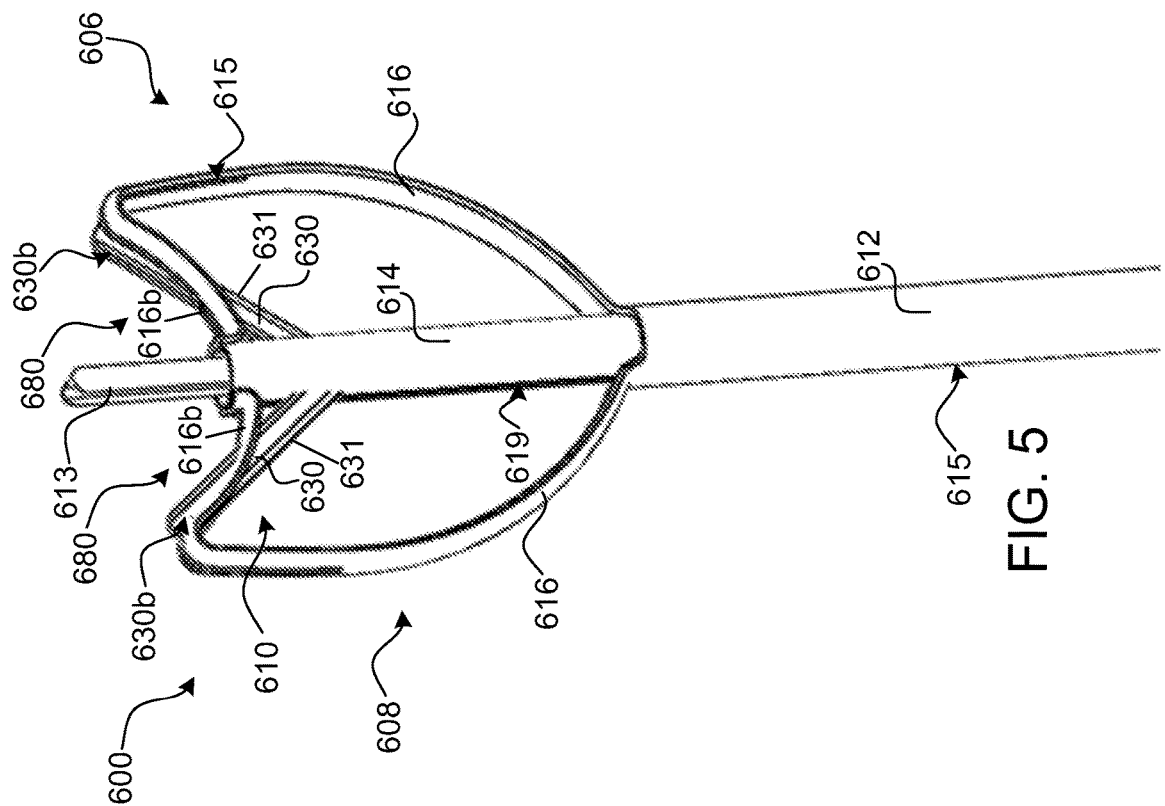
FIGS. 4 and 5 are isometric views of a distal portion of an intraluminal tissue modifying system configured in accordance with the present technology, shown in a first deployed state and a second deployed state, respectively.
Figure 5:
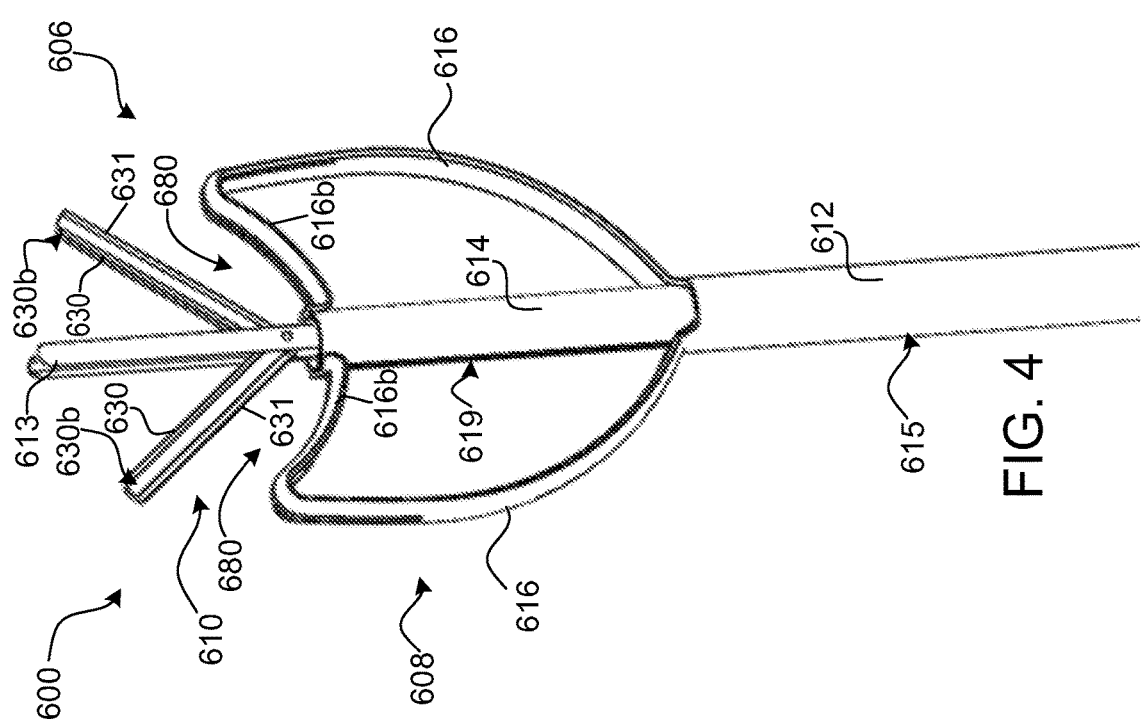

FIGS. 4 and 5 show yet another embodiment of an intraluminal tissue modifying system 600 configured in accordance with the present technology. In FIGS. 4 and 5, the system 600 is shown in a first deployed state and a second deployed state, respectively. The components of the modifying system 600 can be generally similar to those of the modifying system 200 shown in FIGS. 2A-2D, except (1) the capture device 608 and cutting device 610 of system 600 form a capture region 680 that faces distally and (2) in use, the capture device 608 is pushed distally to capture and tension tissue for cutting. Once the tissue has been captured, the cutting device 610 can be deployed or expanded distal to the capture device 608, as shown in FIG. 4. As shown in FIG. 5, the blades 630 of the cutting device 610 can then be pulled proximally into the capture device 608 to cut the intraluminal tissue. In other embodiments, the capture device 608 may be utilized with the distally-facing cutting device 310 shown in FIGS. 3A and 3B.

Figure 6:
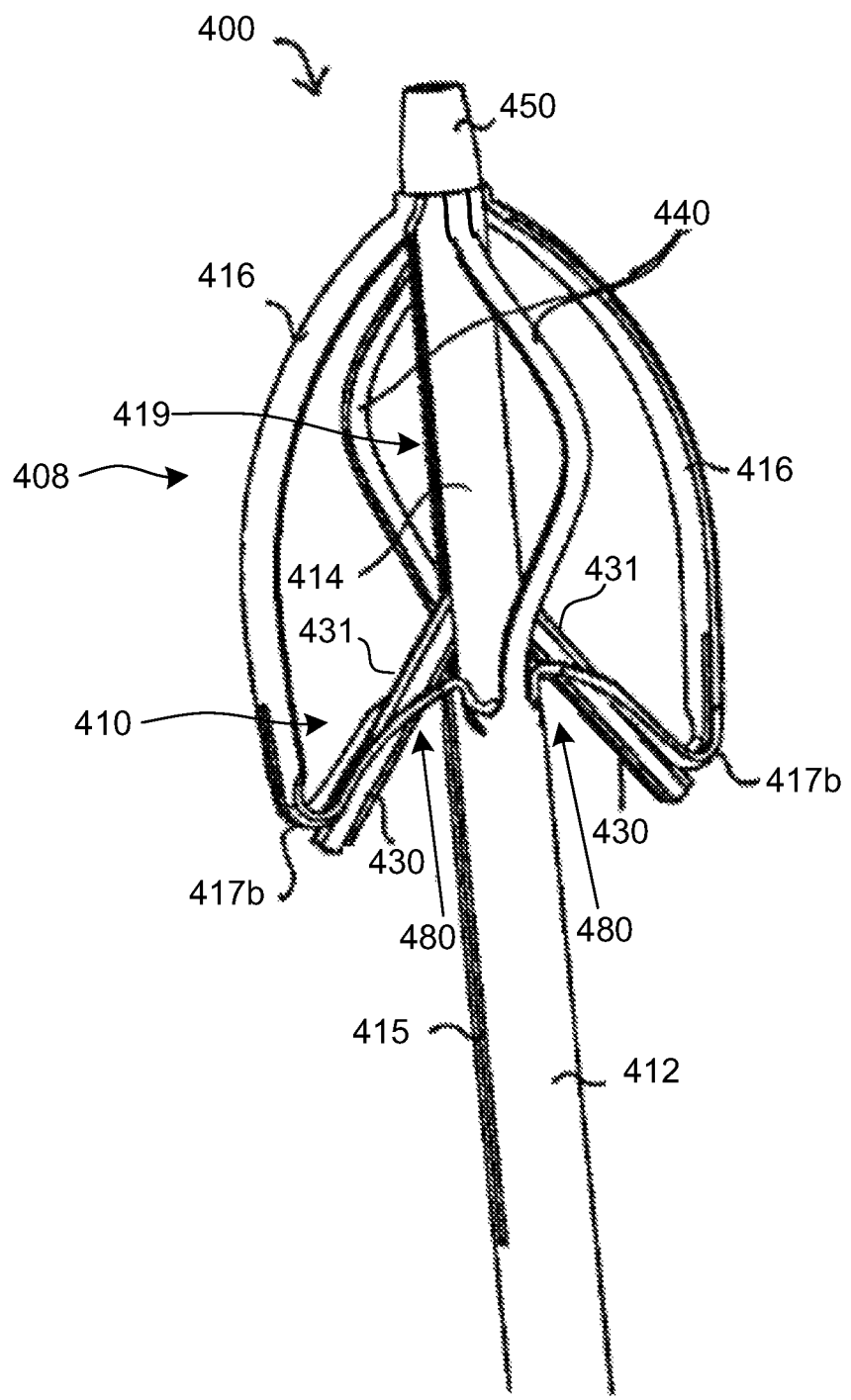
FIG. 6 is an isometric view of a distal portion of another embodiment of an intraluminal tissue modifying system having tensioning arms configured in accordance with the present technology shown in a deployed state.

One advantage of the intraluminal tissue modifying systems of the present technology over conventional devices is that the modifying systems disclosed herein place the vessel wall (e.g., a vein wall) and intraluminal tissue in tension prior to cutting tissue. In some embodiments modifying systems herein, the tissue modifying region can include tensioning arms to provide additional radial tension. For example, FIG. 6 shows an embodiment of an intraluminal tissue modifying system 400 having tensioning arms 440 coupled to the outer shaft 412. (Like numerals in FIG. 6 refer to like parts of the embodiment of FIGS. 2A-2D). In other embodiments, the tensioning arms 440 can be separate components and/or may be coupled to the inner shaft 414 and/or the shaft (not visible) of the cutting device 410. The additional tensioning arms 440 may aid in cutting tissue, especially in vessels that have particularly bulky and/or tough fibrous tissue. In some embodiments, the tensioning arms 440 may be configured to expand radially wider than the capture members 416, thereby reducing the chance of the cutting devices cutting the natural vessel wall during the cutting stage.

In any of the embodiments disclosed herein, the capture device and/or the capture members may be made from a pair of coaxial tubes. For example, in some embodiments the outer shaft and capture members may be formed of a cut outer tube and the intermediate shaft is a tube slidably disposed within the outer shaft such that axial movement of the intermediate shaft relative to the outer shaft (or vice versa) triggers deployment of the capture members. In such embodiments, the outer shaft can be made of a material and have a configuration that is appropriate for being expanded from a straight profile to an expanded lateral or bi-lateral hook shape. Examples of suitable materials include flexible polymers such as nylons, polyethylene, polypropylene, and other polymers appropriate for living hinges, and/or combinations of any of the foregoing materials, which may include other polymers or fillers as appropriate to achieve the desired mechanical characteristics. In certain embodiments, one or more components of the capture device may be made of a flexible or superelastic metal, such as nitinol. The thickness of the tube may determine the strength of the capture device. For example, the polymer materials utilized may not be as stiff and therefore a tube wall thickness may be required to make a capture device with equivalent mechanical properties as one made from a nitinol hook. The cuts are configured such that when the tube is shortened (via, for example, an inner actuator tube), the capture members form an outwardly expanding hook shape. In an embodiment, the struts/capture members form a "bi-stable geometry"; in other words, the struts are geometrically stable in either the collapsed state or in the fully expanded state when the tube is shortened and the proximal section of the struts have swung out past 90 degrees (which would occur if one section is longer than the other). The cut tube may also be heat set to a hooked shape, to facilitate and encourage the tube to assume the hook shape when it is shortened.

Figure 7C:
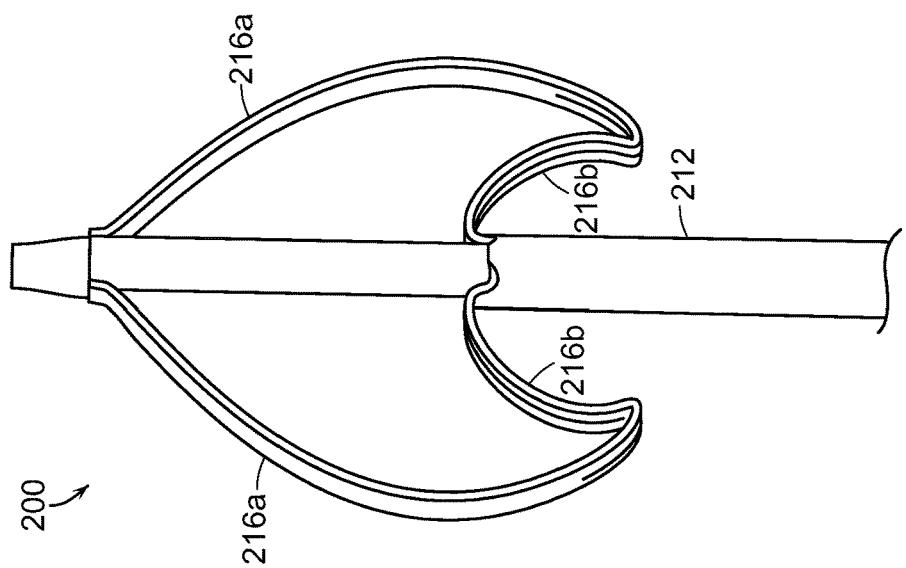
FIGS. 7A-7C show several embodiments of intraluminal tissue modifying systems having capture members with different shapes in the deployed state.
Figure 7B:
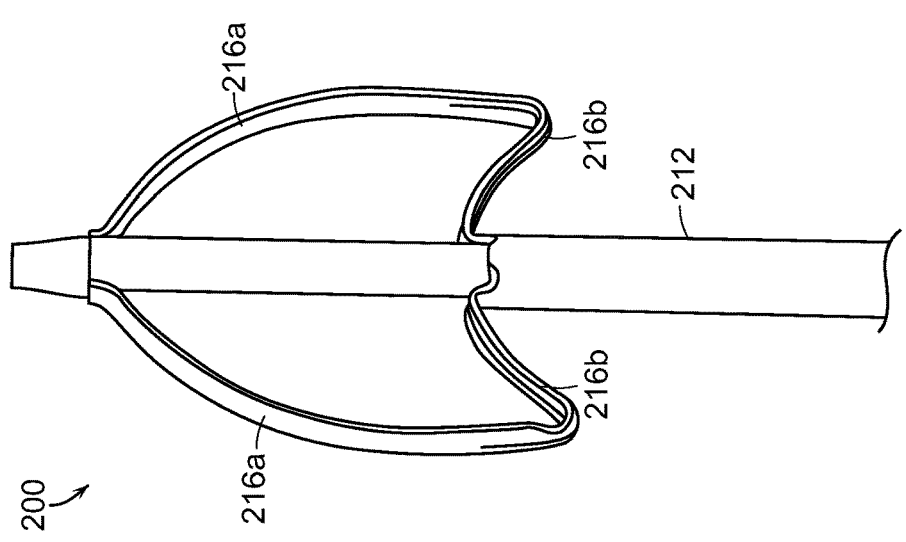
Figure 7A:
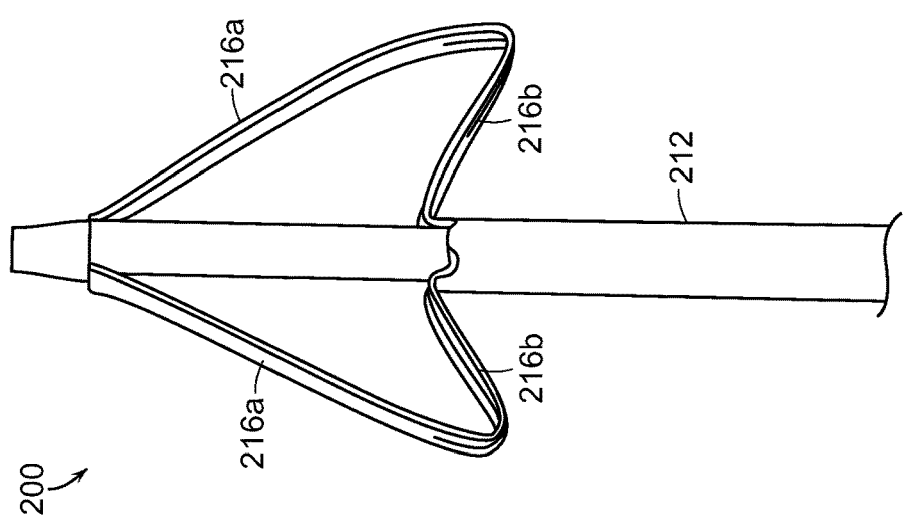

The capture members of any of the capture devices disclosed herein can have any suitable size and/or shape based on a desired bending stiffness, angle, and radius of curvature. For example, FIGS. 7A-7C show several embodiments of capture members having different deployed shapes. In FIG. 7A, both the proximal segment 216b and the distal segment 216a of each of the capture members 216 is relatively straight, and angled radially inwardly. In FIG. 7B, the proximal segments 216a of the capture members 216 droop in a proximal direction. In FIG. 7C, the capture members 216 are configured such that both the distal and proximal segments 216a, 216b curve outwardly away from the longitudinal axis of the outer shaft 212, and then curve radially inwardly back towards the longitudinal axis of the outer shaft 212.

Moreover, the number of segments 201, the length of each segment 201, the angle between segments 201, and/or the shape of each segment 201 (e.g., linear, curved, etc.) can be varied along a single capture member and/or amongst a plurality of capture members. Additionally, in some embodiments, the capture members 216 may be separate components coupled to the outer shaft 212. Furthermore, the deployed shape of the capture members 216 and/or the amount of tissue separated by the capture members 216 may be adjusted by varying the distance traveled by the inner shaft 214 relative to the outer shaft 212 (or vice versa). Also, the cut edges of the outer shaft 212 can be rounded, for example by electropolishing the components.

Figure 8A:
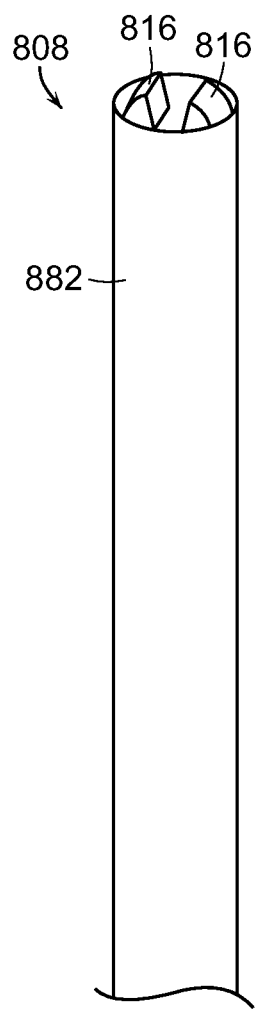
FIGS. 8A and 8B are isometric views of a distal portion of a capture device configured in accordance with the present technology, shown in a low-profile state and a deployed state, respectively.
Figure 8B:
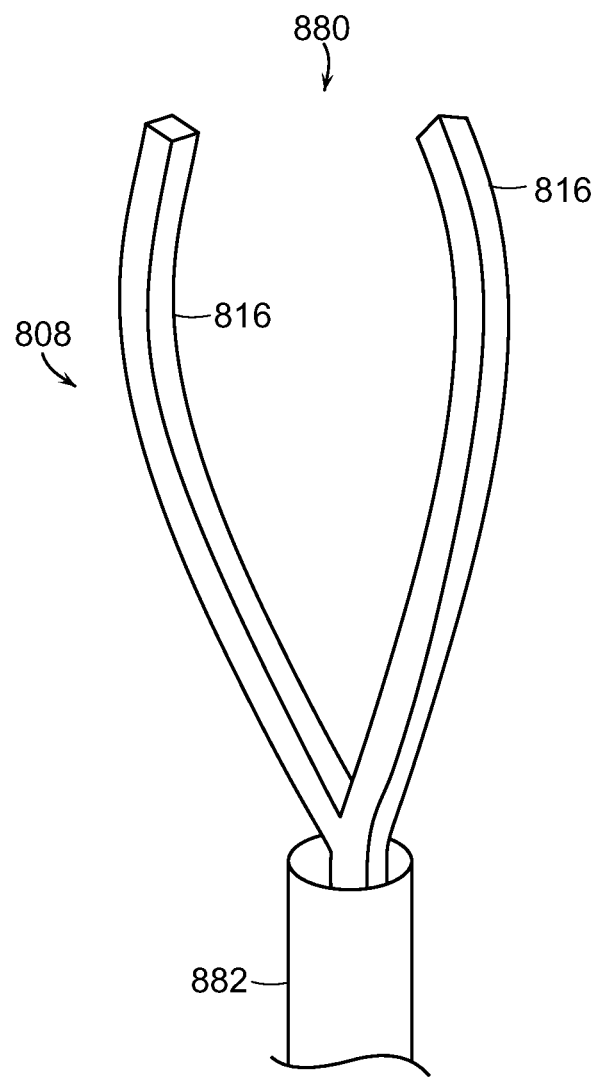

In some embodiments of the present technology, the capture device is a self-expanding member made from spring material such as nitinol or spring steel. For example, FIG. 8A shows one embodiment of a capture device 808 constrained by a retaining sleeve 882 during deployment. When the capture device 808 is at the target treatment site, the retaining sleeve 882 is pulled back (FIG. 8B), allowing the arms or capture members 816 of the capture device 808 to expand outwardly. A cutting device (not shown) may then be expanded distal to the capture device 808 and pulled proximally towards the capture device 808 to cut tissue captured within the capture region 880.

Figure 10:
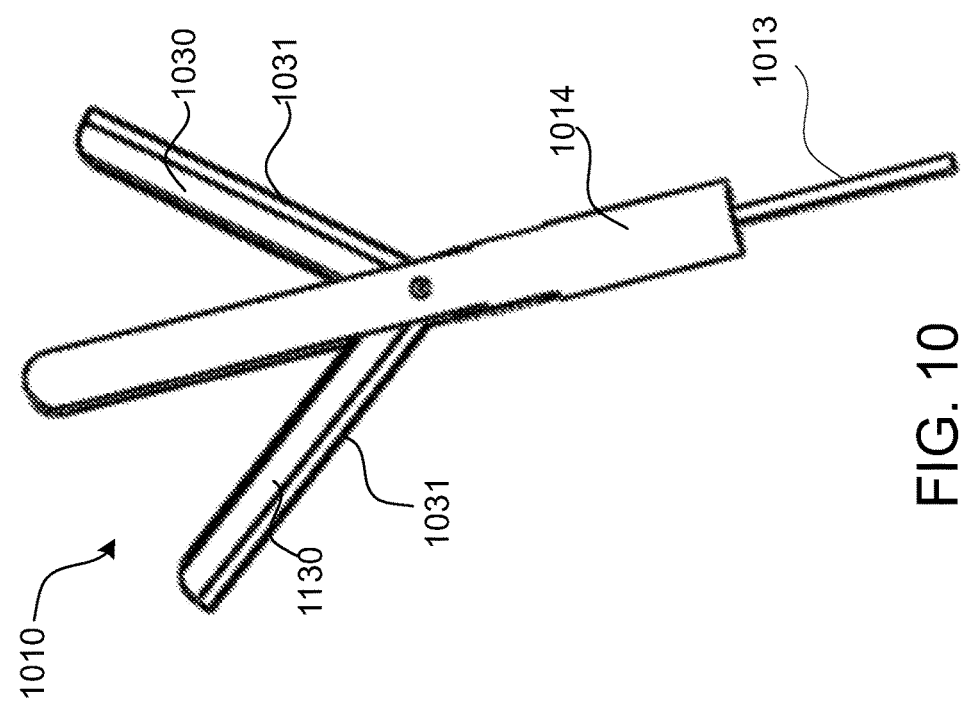
FIG. 10 is an isometric view of a distal portion of a cutting device configured in accordance with the present technology, shown in a deployed state.

Embodiments of cutting devices will now be described in detail. FIG. 9A shows one embodiment of a cutting device 910 comprised two blades 930 that can be transformable between from a low-profile state (not shown) and a deployed or expanded state (as shown in FIG. 9A). In other embodiments, the cutting device 910 can include more or fewer blades (e.g., one blade, three blades, four blades, etc.) As shown in FIG. 9A, the blades 930 are coupled to an elongated shaft 913 and an elongated member 940 (such as a pull or push rod) slidably received within a lumen of the elongated shaft 913. FIG. 9B shows an isolated view of the blades 930 and inner member 940, and FIG. 9C shows an enlarged view of a portion FIG. 9B. Referring to FIGS. 9B and 9C together, each of the blades 930 are rotatably coupled to the outer shaft 913 via a first pin 943 (or other coupling device(s)) that extends from one side the shaft 913 across the gap 942 through the thickness of each of the blades 930 and a slot 944 along the attachment region 946 of the inner member 940, and is fixed at an opposing side of the shaft 913. One end of the first pin 943 sits within. The cutting device 910 further includes second pins 941a, 941b (or other coupling device(s)), each of which extend through (and/or from) the corresponding blade 930 and through a corresponding slot 945a, 945b, respectively, along a distal coupling region 946 of the inner member 940. When the inner member 940 is moved axially with respect to the shaft 913, the second pins 941a, 941b push the blades 930 axially while the blades 930 rotate around the first pin 943. Similar mechanisms can be used for blades that are oriented in an opposite direction (e.g., with the sharpened edge of the blades facing proximally), as shown in the cutting device 1010 of FIG. 10. Other actuation mechanisms are also possible to move the blades from a low-profile state to a deployed or expanded state.

Figure 11:
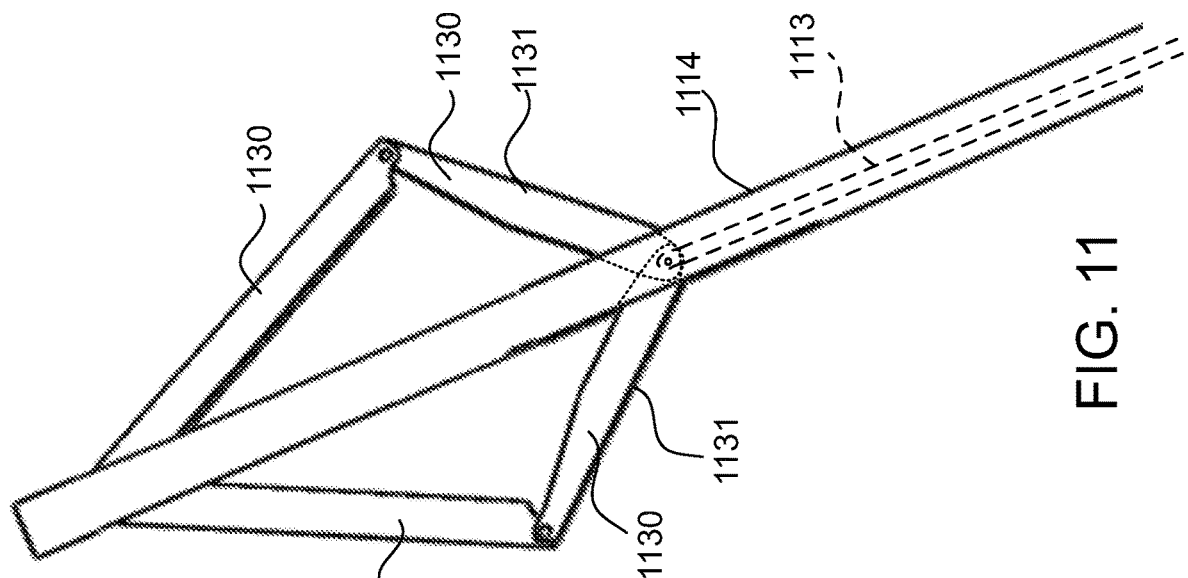
FIG. 11 is an isometric view of a distal portion of another embodiment of a cutting device configured in accordance with the present technology, shown in a deployed state

Another embodiment of a cutting device is shown in FIG. 11. In this embodiment, the blades 1130 are attached to secondary support arms 1131 to add strength and rigidity to the blades during the cutting stage. When opened, the blades 1130 and support arms 1131 form a diamond shape. In some embodiments, both the distal and proximal segments of the diamond may have cutting edges, so that the cutting device 1110 can cut both forwards (in a distal direction) and backwards (in a proximal direction) into and out of the capture device. This configuration may allow a "saw" like cutting motion to cut longer or more tougher sections of captured tissue, such as fibrotic septums. The cutting device 1110 may be used in a proximal-facing modifying systems (such as systems 200 and 300) and/or distal-facing systems (such as system 600).

Figure 12A:
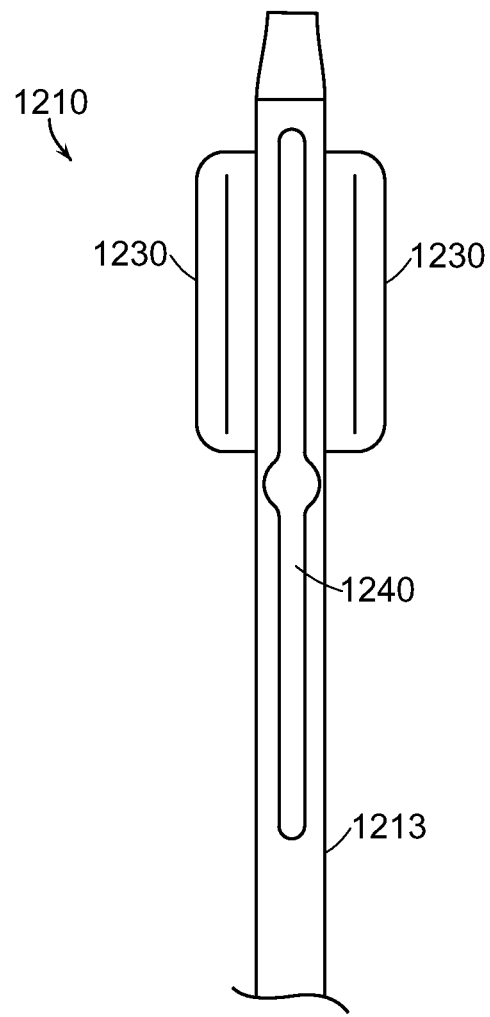
FIGS. 12A and 12B are isometric views of a distal portion of a cutting device configured in accordance with the present technology, shown in a low-profile state and a deployed state, respectively.
Figure 12B:
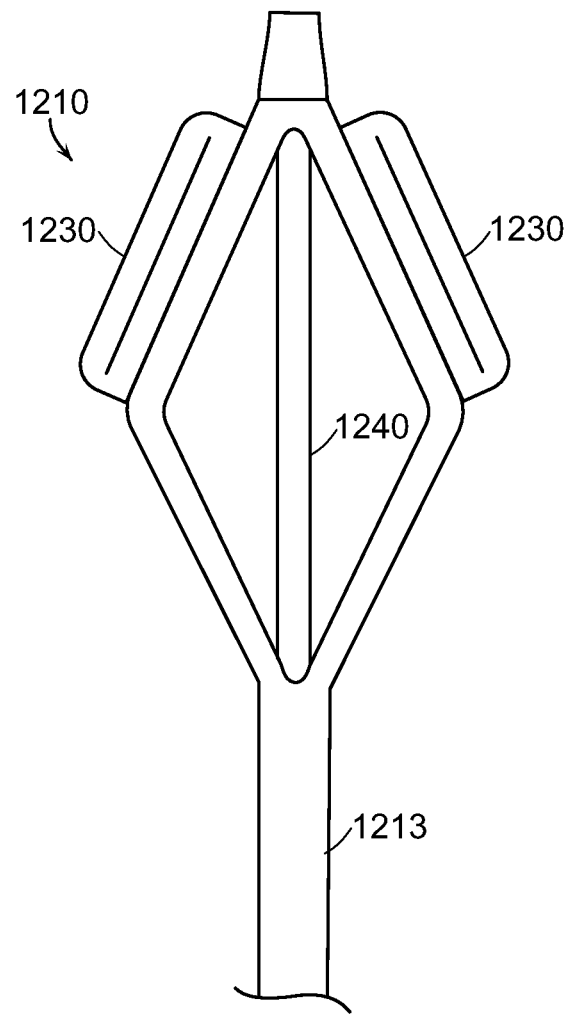

Yet another embodiment of a cutting device is shown in FIGS. 12A and 12B. In this embodiment, the blades 1230 are attached to expandable members formed from a cut tube 1213. An inner actuator tube 1240 pushes the blades 1230 outward, as seen in FIG. 12B. The blades 1230 may be attached to the expandable members of cut tube 1213 via soldering, welding, etc. Alternately, the blades 1230 may be attached mechanically, for example via features such as hooks formed on the attachment side of blade 1230 corresponding with slots on the cut tube 1213 and configured such that the hooks lock securely into place when positioned in the slots. A variation of this embodiment is shown in the cutting device 1310 of FIGS. 13A-13B. In this embodiment, the blades 1330 are attached at only one end, and angled outward when the outer cut tube 1313 is shortened or deployed via the cutting device actuator tube 1340. Both of the cutting devices 1210 and 1310 have the advantage that they can maintain an inner lumen, and thus not require removal of an inner element such as a guide wire or imaging catheter during the cutting of the tissue.

FIGS. 14A-14C show another embodiment of a cutting device 1410 configured in accordance with the present technology. The cutting device 1410 utilizes energy to perform the cutting function. In the embodiment shown in FIGS. 14A-14C, the cutting device 1410 includes an expandable wire structure 1450 connected to an energy source 1452 (shown schematically), such as radiofrequency (RF) energy, ultrasound energy, plasma energy, and/or other suitable energy sources that can cut through tissue on contact. The cutting device 1410 can also include an outer shaft 1412 and an inner actuator 1440 (e.g., solid rod, hollow tube, etc.) that are coupled at their respective distal portions. As shown in FIG. 14B, the wire structure 1450 may be foreshortened via proximal movement of the inner actuator 1440 that expands the wire structure outwardly away from the longitudinal axis of the inner actuator 1440. In this expanded or deployed state, the wire structure 1450 is then energized and pulled towards the capture device (not shown) to cut the tissue. FIG. 14C shows a variation of the embodiment shown in FIGS. 14A-14B. In FIG. 14C, the wire structure 1450 is selectively insulated, for example, with an outer coating or insulation layer 1458, to limit the exposed cutting portion of the wire structure 1450.

Any of the cutting devices (or combinations thereof) may be used with any of the capture devices described herein as appropriate to perform an intraluminal tissue capture and cutting procedure.

In some embodiments of the intraluminal tissue modifying systems disclosed herein, the capture device and the cutting device may be integrated into a single device such that the tissue capture and cutting may occur in a single step. Such a tissue modifying system may require less components than, for example, the system 200 shown in FIGS. 2A-2D, and as a result, system 1500 may have a smaller profile. FIGS. 15A and 15B, for example, show an intraluminal tissue modifying system 1500 (or "system 1500") having a combined capture/cutting device 1507, shown in a low-profile delivery state and a deployed state, respectively. The components of the tissue modifying system 1500 can be generally similar to the components shown in FIGS. 2A-2D, except the system 1500 does not include a separate cutting device and instead the capture members 1516 include cutting elements 1530 positioned along their proximal segments 1516b. In some embodiments, one or more of the cutting elements 1530 may be separate components (e.g., blades) that are attached to the capture members 1516 via soldering, welding, gluing, or other attachment devices. In these and other embodiments, one or more of the cutting elements 1530 may be integral with/formed of the outer shaft 1512 (e.g., not a separate component) and/or capture members 1516.

Figure 16:
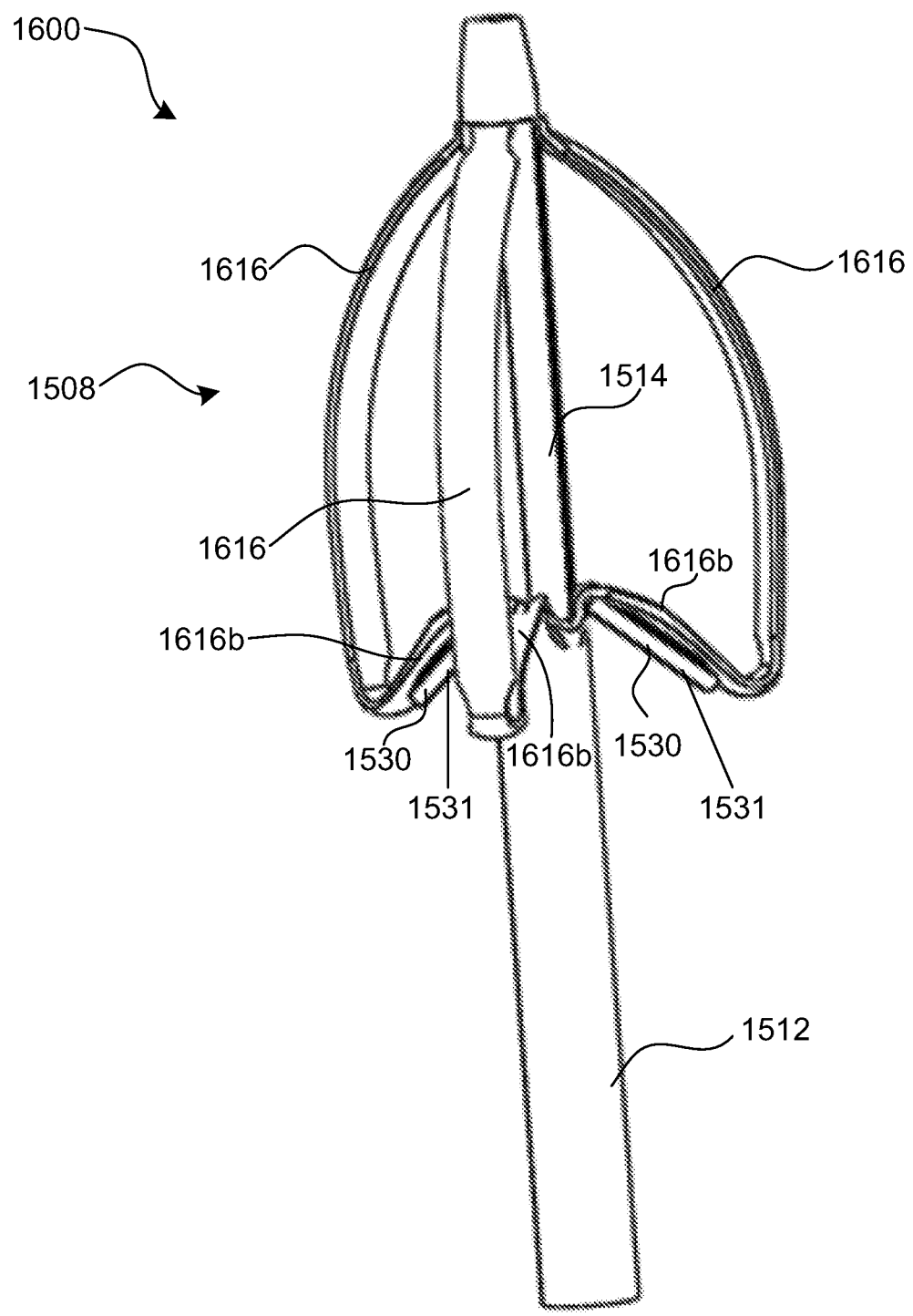
FIG. 16 is an isometric view of a distal portion of another embodiment of an intraluminal tissue modifying system having tensioning arms configured in accordance with the present technology shown in a deployed state.

The cutting elements 1530 may be attached or integrated with all or some of the capture members 1516. Moreover, although the tissue modifying system 1500 is shown having two capture members 1516, in other embodiments the tissue modifying system 1500 may have more or fewer capture members (e.g., a single capture member, three capture members, four capture members, five capture members, etc.). For example, FIG. 16 shows an intraluminal tissue modifying system 1600 generally similar to the tissue modifying system 1500, except system 1600 has three capture members 1616, all of which individually include a cutting element 1530 positioned along their respective proximal segments 1616*b*.

In some embodiments, the system can include a cutting device attached to the inner capture member surface which is an energized element, such as an RF, plasma, or ultrasonic electrode. In this embodiment, the energy may be applied after the intraluminal tissue has been captured and put into tension by the capture member.

In any of the embodiments of intraluminal tissue modifying systems disclosed herein, the capture device and/or cutting device may have an internal lumen that is sized to accommodate a guidewire and/or a catheter (e.g., a guidewire and/or catheter having a 0.035" outer diameter, a guidewire and/or catheter having a 0.038" outer diameter, etc.). In such embodiments, the system may be delivered over the guidewire and/or a catheter to a target treatment site, and may sub-selectively guide an interventional catheter and/or imaging catheter during the procedure. Examples of suitable catheters include imaging catheters, such as intravascular ultrasound (IVUS) catheters, optical coherence tomography (OCT) catheters, angioscopes, and/or other imaging modality, and interventional catheters, such as balloon catheters, stent delivery systems, diagnostic angiographic catheters, thrombectomy catheters, and the like. Once the tissue modifying system is positioned at the treatment site (and/or sub-component thereof, such as a capture device and/or a cutting device), the guidewire can be removed and replaced with a cutting device (for example, if the cutting device does not have a central lumen, such as the cutting device 210 shown in FIGS. 2A and 2B), an imaging catheter, and/or an interventional catheter as needed to capture, cut, and/or otherwise modify tissue at the treatment site. In those embodiments where the cutting device does have a central lumen, the tissue cutting step can be performed without the need to exchange the guidewire for a cutting device. In these embodiments, the guidewire may still be exchanged for another catheter such as a balloon catheter or stent delivery catheter for further tissue modification at the treatment site or nearby site.

FIG. 17 shows another embodiment of an intraluminal modifying system 1700 configured in accordance with the present technology. In FIG. 17, the system 1700 is shown positioned in a blood vessel V. The components of system 1700 can be generally similar to the components of system 200 shown in FIGS. 2A-2D, except the system 1700 includes a distal occlusion balloon delivered through the lumen of the intermediate shaft 1714 and configured to block blood flow in the vessel V. As shown in FIG. 17, the system 1700 can be used with an angioscopic imaging catheter 1790. Clear saline may be delivered to the target site (e.g., via a central lumen, an introducer sheath, a guide catheter, etc.). An angioscope 1790 may be placed alongside the system 1700 and used to visualize the intraluminal fibers during the capture and cutting stages. Alternately, as shown in FIG. 18, the angioscope may be delivered via a distal access site along with an occlusion balloon to provide a view from distal to proximal of the treatment site.

Figure 19:
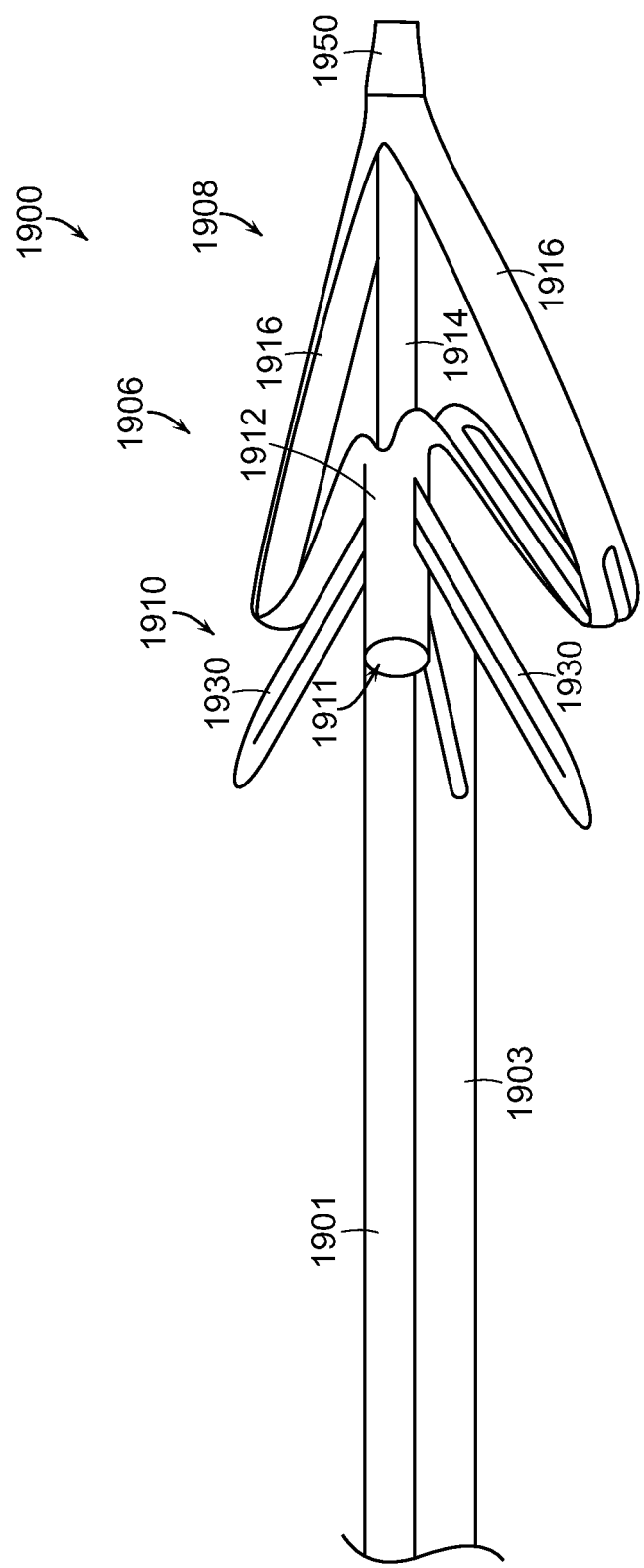
FIG. 19 shows another embodiment of an intraluminal tissue modifying system configured in accordance with the present technology.

In some embodiments, the intraluminal tissue modifying system may have a lumen alongside the main actuation shaft. FIG. 19 depicts an embodiment of an intraluminal tissue modifying system 1900 with a lumen 1902 running parallel to a main actuation shaft 1910, and a tissue modifying region 1906 at the distal portion of the main actuation shaft 1910. This lumen 1902 is configured to function as a lumen to deliver an imaging and/or interventional catheter to the treatment site. In one version of this embodiment, the lumen 1902 runs the entire length of the system from distal tip to proximal handle. As depicted in FIG. 19, the lumen 1902 terminates distally at an opening 1911 that is proximal to the tissue modifying region 1906. A port on the proximal handle is attached to the proximal end portion of lumen 1902, and terminates on the proximal end by a hemostasis valve to allow safe introduction of devices in and out of this lumen. This lumen may also be used for contract injection, flushing, and delivery of therapeutic agents such as thrombolytic agents. The addition of a lumen to the system may increase the cross-sectional area of the device, but increases functionality of the system. It allows maintenance of guidewire access across the target site during the cutting stage, and/or allows peri-procedural imaging from an intravascular imaging device.

FIGS. 20A and 20B show another embodiment of an intraluminal tissue modifying system 2000 configured in accordance with the present technology. The system 2000 has a second lumen 2002 which runs alongside the length of the device including the distal section, and is then rejoined to a first lumen 2004 at a distal portion of the device. This version allows for simultaneous imaging during the tissue capture and tissue cutting stages of the procedure, thus providing a more accurate and reliable procedure. In this embodiment, the system 2000 has the first lumen 2004 through the main actuation shaft, and the second lumen 2002 which combines with the first lumen 2004 just proximal to the distal portion to create a single distal lumen 2006, such that there are two lumens in the system for the entire length of the system except for the portion of the distal region that is axially aligned with the interior region of the capture members 2016 in a deployed state. In use, the system 2000 is inserted over a guidewire 2090, which is disposed in the first lumen 2004 and continues through the distal/combined lumen 2006 and out the distal tip, as depicted in FIG. 20A. The cutting device is retracted so that it is fully in the second lumen 2002. One positioned, the capture members 2016 may be expanded outward to tension the desired tissue. The guidewire 2090 is then pulled back so that it is fully in the second lumen 2002. The cutting device 2010 can now be advanced forward from the first lumen 2004 to the distal lumen 2006 through the center of the expandable capture device 2008, and perform a cutting stage. This version has a smaller crossing profile, which is desirable in some instances.

Figure 21:
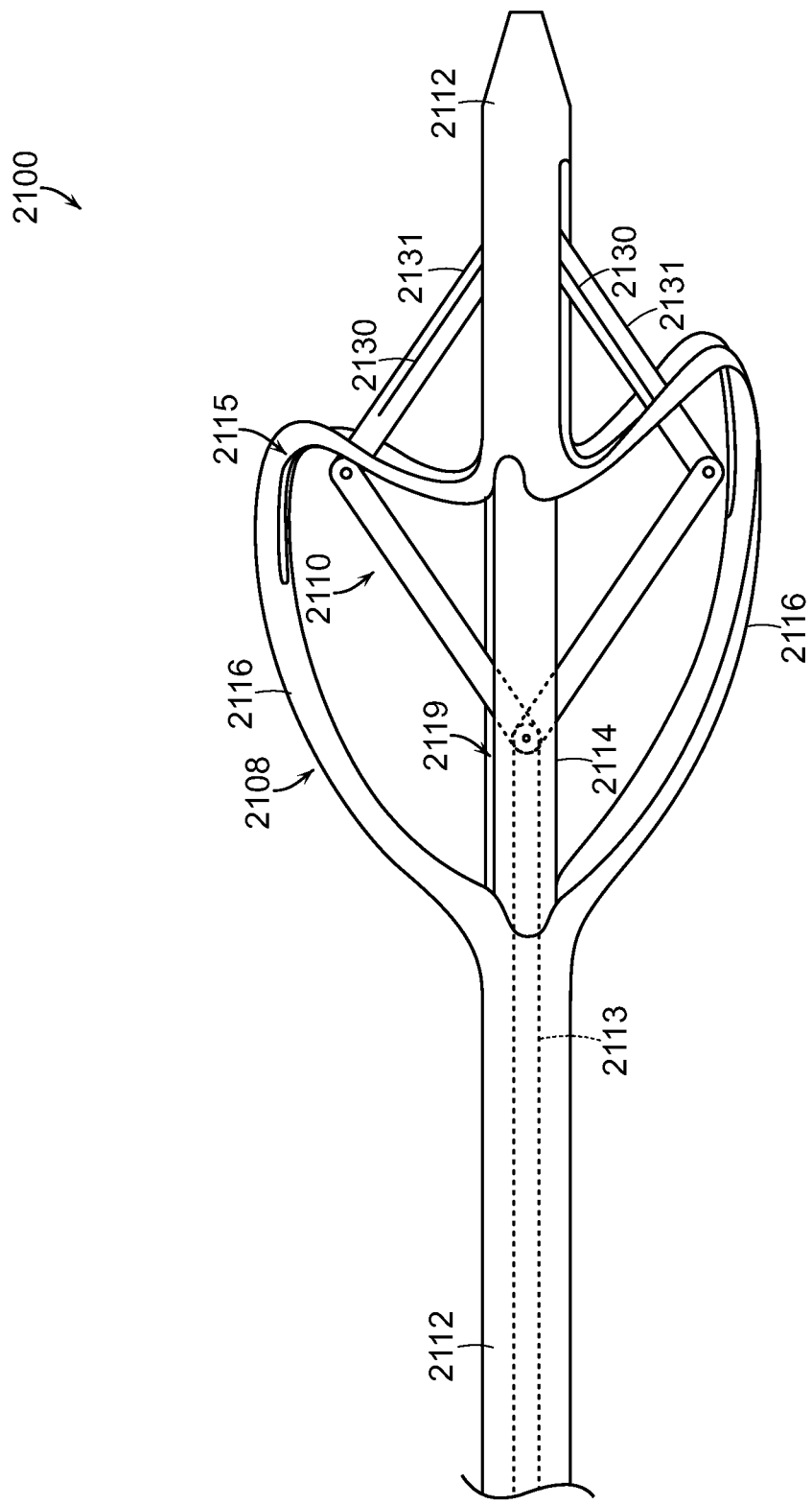
FIG. 21 shows another embodiment of an intraluminal tissue modifying system configured in accordance with the present technology.

Another embodiment of an intraluminal tissue modifying system is shown in FIG. 21. The tissue modifying system 2100 includes a distal-facing capture device 2108 (generally similar to the capture device 608 shown and described with respect to FIGS. 4 and 5) and a two-sided cutting device 2110 with blades 2130 configured in a diamond shape (generally similar to the cutting device 1110 shown and described with respect to FIG. 11). The cutting edges 2131 of the blades 2130 extend distal to the capture members 2116 and are guided by a section of outer shaft 2112 that extends distal to the capture members 2116. Slots 2115 in the outer shaft 2112 and capture members 2116 allow the blades 2130 to cut and move/slide through the capture device 2108. The cutting device 2110 may be moved axially in both proximal and distal directions to cut tissue in both directions while the tissue is being held in tension with the capture members 2116.

FIGS. 22A-22C illustrate a variation of the embodiments shown in FIGS. 20A and 20B and FIG. 21. The intraluminal tissue modifying system 2200 of FIGS. 22A-22C includes an additional shaft 2203 running parallel to the outer shaft 2212 along at least a portion of its length. The shaft 2203 includes lumen 2204 (FIG. 22B). The lumen 2204 of the shaft 2203 combines with the lumen 2222 of the outer shaft 2212 at a distal portion of the modifying system 2200 to form lumen 2206 (FIG. 22C). The lumens 2204 and 2222 may combine, for example, at a location that is distal to a distal end of the slots 2215 in the outer shaft 2112. The lumen 2204 may be configured to slidably receive a guidewire 2290 therethrough (e.g., a 0.035" or 0.038" guidewire), such that the system 2200 may be delivered over the guidewire 2290 to a target site before and/or during the capture and cutting stages of the procedure.

In yet another embodiment, the system has a second lumen for a guidewire and a third lumen for imaging or interventional device. In this version, the cutting device and imaging can happen simultaneously while maintaining guidewire access across the target site. Similar to above, all three lumens may run the entire length of the device. Alternatively, the three lumens may combine into one lumen proximal to the distal section, so that different elements can be advanced or pulled back as required during system access, peri-procedural or post-procedural stages. Alternatively, the guidewire lumen and the cutting lumen can combine into one lumen distally into one lumen at the distal tip of the device, but the third imaging lumen remains a separate lumen throughout the entirety of the device. Alternatively, the guidewire lumen and the cutting lumen can combine into one lumen distally into one lumen at the distal tip of the device, but the third imaging lumen terminates proximal to the distal section of the device, so that imaging can be performed around the cutting and capture sections of the device. Alternatively, the guidewire lumen and the cutting lumen can combine into one lumen distally into one lumen at the distal tip of the device, but the third imaging lumen contains a "window" or material specially designed to be imaged there through near the distal section as described previously.

In any of the embodiments which including intravascular imaging capabilities, the lumen for the imaging catheter is configured to minimize interference with obtaining a good image. For example, materials used to create the lumen can be constructed from echolucent or radiolucent materials, or alternately "windows" are cut out of the lumen wall at the appropriate section. In some embodiments a "window" or section specifically designed for imaging therethrough is placed specifically at a location along the length of the device that corresponds with the capture members' curved joints when the capture device is in the deployed or expanded state. In other embodiments, the "window" or section specifically designed for imaging therethrough spans a length that extends proximal to and distal to the length of the device that corresponds with the capture members' curved hinge points when the device is in the deployed or expanded state. These embodiments have the advantage of allowing the user of the device to image the tissue to be captured around the same section of vein where the capture devices reside, so that the device can be rotated to an appropriate angle to more effectively capture the tissue.

All embodiments describing different configurations of multiple lumens apply to systems having or configured to receive proximal-facing cutting devices and/or systems having or configured to receive distal-facing cutting devices.

Figure 23:
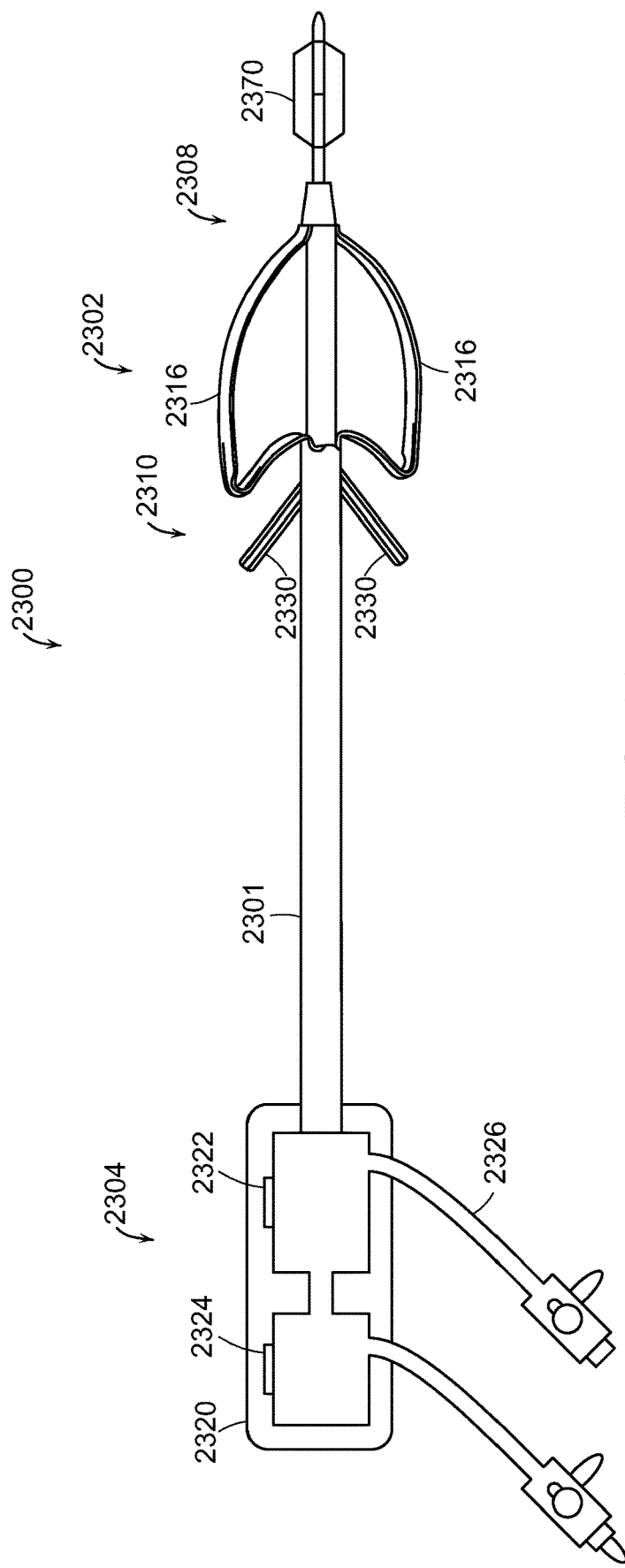
FIG. 23 is a partially schematic overview of an intraluminal tissue modifying system configured in accordance with the present technology, shown in a deployed state.

In some procedures, it may be desirable to utilize an expandable member while cutting tissue. In this instance, the tissue cutting stage may be a beneficial pre-procedural stage before balloon dilatation of an obstructed or partially obstructed vein. As described above, the system may have a lumen which can be used to deliver a catheter having an expandable member, such as a balloon or expandable cage, to the site where venous synechiae has been cut through by the capture and cutting stages. In another embodiment, as shown in FIG. 23, the system 2300 has an expandable member, such as an inflatable dilatation balloon element 2370, slidably or permanently attached to the system. As shown in FIG. 23, the dilatation balloon element 2370 may be positioned distal to the capture device 2308. Alternately, the dilatation balloon element 2370 may be positioned proximal to the capture device 2308. The dilatation balloon element 2370 can be moved distally or proximally after the cutting stage to perform a balloon dilatation step without needing to exchange devices and re-access the treatment site during the procedure. In this embodiment, the system 2300 has an additional lumen to couple the expandable member 2370 to an actuator. For example, in those embodiments where the expandable member 2370 is a balloon, the additional lumen may be an inflation lumen coupled to a pressure-generating device. The balloon material may be non-compliant, semi-compliant, or compliant, to be used for either dilatation of the vessel or occlusion of the vessel, for example when used in conjunction with an angioscope, or to be used for both purposes during different parts of the procedure. Examples of non-compliant or semi-compliant balloon materials include polyethylene, nylon, polyurethane, polyamides or blends of these materials. Examples of compliant balloon materials include low durometer polyurethanes, silicone rubber, latex, or blends of these materials. In those embodiments where the expandable member 2370 is an expandable cage (e.g., a nitinol cage), a pull-wire or push rod or other connecting member may extend distally from the handle 2320 through the additional lumen 2327 to the expandable cage at the distal portion of the system 2320.

Any of the systems disclosed herein may be configured to treat a range of vessel sizes. For example, in some embodiments the system can be configured to treat veins having an inner diameter from about 5 mm to about 35 mm. In another embodiment, the system comes in a range of sizes, each able to treat a corresponding vein inner diameter range, for example a small size system can treat veins from about 5 mm to about 12 mm, a large size can treat veins about 10 mm to about 18 mm, and yet a third size can treat about 15 mm to about 23 mm. As is noted, the size ranges overlap so that there is a greater possibility that only one device size can be used to treat a patient with a range of vein sizes. In another example, two sizes of systems can treat two overlapping ranges of vein sizes that covers the desired range of vessels to be treated.

Disclosed now are methods of use of this system. In a first stage, the intravascular tissue modifying system is inserted into a vein and advanced to a target treatment site over a 0.035" guidewire. The system may be inserted from a femoral vein and advanced in a retrograde fashion to a target leg vein. Alternatively, the system may be inserted in a distal leg vein, for example a tibial or popliteal vein, and advanced in an antegrade fashion to a target site.

Once at or near the target site, the guidewire may be exchanged for an intravascular imaging catheter. The system may be guided over the imaging catheter to the target site, using the imaging information. In the embodiment with two or more lumens, the guidewire may remain in place or be pulled back out of the distal portion and the imaging catheter is advanced. Alternately, an imaging catheter may be placed side by side with the system at the target site to aid in positioning. In an embodiment, the imaging system is angioscope. In this method embodiment, as shown in FIG. 17, the central lumen may be used to deliver a balloon catheter and provides occlusion to blood flow to allow flushing the treatment area with clear saline. Alternately, the system has an integrated or built-in balloon catheter to perform the occlusion function. Alternately, as a balloon catheter is delivered via a distal access site and advanced to a position distal to the treatment site to provide blood occlusion as required to create a clear viewing area for the angioscope. The angioscope may be positioned side by side with the system in the vessel through the same introducer sheath, or be delivered through a secondary lumen in the system. Alternately, as shown in FIG. 18, the angioscope may be delivered via a distal access site along with an occlusion balloon to provide a view from distal to proximal of the treatment site.

In a second stage, the expandable capture device is expanded and gently pulled proximally until resistance is met. Capture of intraluminal tissue may be confirmed via the imaging catheter, external ultrasound, and/or tactile feedback of resistance to movement.

In a third stage, a cutting device is advanced and expanded. In the embodiment with a single internal lumen, the imaging catheter is removed to advance the cutting device. Alternately, in other embodiments, the imaging catheter may remain in place or positioned next to the system during cutting device advancement. Once the cutting device is expanded, it can be pulled back (proximally) towards the capture device to cut intraluminal tissue. Additional capture and cutting stages may be performed in the same or different target sites in the veins, using intravascular and external imaging methods as guidance to complete sufficient excision of the intraluminal tissue.

Variations of capture and cutting stages are possible with different embodiments. Additional interventions such as balloon dilatation or stent implantation may be performed during or after the tissue cutting stages in the same procedure.

In the embodiment with a combined tissue cutting and balloon dilatation device, once the tissue is cut the balloon is positioned at the target site and a balloon is inflated to perform a vessel dilatation stage. Tissue cutting and balloon dilatation may be repeated as necessary to achieve a desired hemodynamic stage.

Imaging modalities such as IVUS, OCT, and/or angioscopy may be utilized as adjuncts to the positioning, capture, and/or cutting stages of the methods disclosed herein.

The devices and systems of the present technology are configured to easily capture and cut through dense and fibrous tissue, partially obstructive tissue in veins, without causing injury to the native vein wall. The devices and systems of the present technology are also configured to put anatomical structures in tension during cutting to improve the accuracy and efficiency of the resulting cut. The devices and systems of the present technology are configured to cut anatomical structures without being pulled out of the target treatment site, so that repeat cuts can be done without having to re-cross or re-access a particular site.

Conclusion

Although many of the embodiments are described above with respect to devices, systems, and methods for intravascular creation of autologous venous valves and/or valve leaflets, other applications and other embodiments in addition to those described herein are within the scope of the technology. For example, the devices, systems, and methods of the present technology can be used in any body cavity or lumen or walls thereof (e.g., arterial blood vessels, venous blood vessels, urological lumens, gastrointestinal lumens, etc.) and used for surgical creation of autologous valves as well as repair of autologous and/or synthetic valves. Additionally, several other embodiments of the technology can have different states, components, or procedures than those described herein. For example, although several embodiments of the present technology include two capture members and/or two blades, in other embodiments the capture device and the cutting device can have more or fewer than two capture members and/or two blades, respectively (e.g., one capture member, three capture members, four capture members, etc.) (e.g., one blade, three blades, four blades, etc.) For example, in some embodiments, the capture device and/or the cutting device can include a single capture member or blade, respectively, having a first portion configured to extend laterally away from the longitudinal axis of the shaft in a first direction and a second portion configured to extend laterally away from the longitudinal axis of the shaft in a second direction opposite the first direction. Moreover, it will be appreciated that specific elements, substructures, advantages, uses, and/or other features of the embodiments described with reference to FIGS. 1-23 can be suitably interchanged, substituted or otherwise configured with one another in accordance with additional embodiments of the present technology. For example, the tensioning arms described with reference to FIG. 6 can be combined with any of the modifying systems disclosed herein. Likewise, the cutting devices described in FIGS. 9A-14C can be combined with any of the capture members, tensioning arms, and/or capture devices described herein.

Furthermore, suitable elements of the embodiments described with reference to FIGS. 1-23 can be used as standalone and/or self-contained devices. A person of ordinary skill in the art, therefore, will accordingly understand that the technology can have other embodiments with additional elements, or the technology can have other embodiments without several of the features shown and described above with reference to FIGS. 1-23. For example, the intraluminal tissue modifying devices, systems, and methods of the present technology can be used with any of the devices, systems, and methods disclosed in U.S. patent application Ser. No. 13/035,752, filed Feb. 2, 2011, U.S. patent application Ser. No. 13/926,886, filed Jun. 25, 2013, U.S. patent application Ser. No. 13/035,919, filed Feb. 25, 2011, U.S. patent application Ser. No. 13/450,432, filed Apr. 19, 2012, U.S. patent application Ser. No. 14/377,492, filed Aug. 7, 2014, PCT Application No. PCT/US2014/011209, filed Jan. 10, 2014, U.S. patent application Ser. No. 14/499,969, filed Sep. 26, 2014, U.S. Provisional Patent Application No. 61/969,262, filed Mar. 24, 2013, U.S. Provisional Patent Application No. 61/969,263, filed Mar. 24, 2013, U.S. patent application Ser. No. 14/759,797, filed Jul. 8, 2015, U.S. patent application Ser. No. 14/498,969, filed Sep. 26, 2014, U.S. patent application Ser. No. 14/667,201, filed Mar. 24, 2015, U.S. patent application Ser. No. 14/667,670, filed Mar. 24, 2015, U.S. patent application Ser. No. 14/972,006, filed Dec. 16, 2015, U.S. Provisional Patent Application No. 62/317,470, filed Apr. 1, 2016, and U.S. Provisional Patent Application No. 62/345,687, filed Jun. 3, 2016, all of which are incorporated by reference herein in their entireties.

We claim:

1. A device for modifying intraluminal tissue, the device comprising:
    a first shaft having a distal portion with a distal end region, and a first lumen extending through the distal portion, wherein the first shaft includes a plurality of capture members extending along a length of the distal portion;
    a second shaft disposed within the first lumen, the second shaft having a distal end region fixed to the distal end region of the first shaft such that proximal movement of the second shaft relative to the first shaft forces each of the plurality of capture members to bend outwardly away from a longitudinal axis of the first shaft; and
    a third shaft extending alongside the first shaft and defining a second lumen along at least a length of the distal portion of the first shaft, wherein the second lumen is spaced laterally apart from the first lumen, and wherein the third shaft is configured to deliver a tool to the distal portion of the first shaft.

2. The device of claim 1 wherein the third shaft is configured to slidably receive a guidewire via the second lumen.

3. The device of claim 1 wherein the first lumen and the second lumen combine to form a singular lumen along the distal end region of the first shaft.

4. The device of claim 1 wherein the third shaft is configured to slidably receive an imaging catheter within the second lumen.

5. The device of claim 4 wherein the third shaft comprises a visualization section positioned along the distal portion of the first shaft, and wherein the visualization section comprises an echolucent and/or radiolucent material to allow the imaging catheter within the second lumen to image the distal portion of the first shaft and/or a region distal to the first shaft.

6. The device of claim 5 wherein the visualization section extends from a first position proximal to the plurality of capture members to a second position that is distal to the plurality of capture members.

7. The device of claim 4 wherein the imaging catheter has an inner lumen configured to slidably receive a guidewire therethrough.

8. The device of claim 1 wherein the third shaft is configured to slidably receive an expandable member via the second lumen.

9. The device of claim 8 wherein the expandable member has an inner lumen configured to slidably receive a guidewire therethrough.

10. The device of claim 1, further comprising a fourth shaft extending along the first shaft and defining a third lumen along at least a length of the distal portion of the first shaft, wherein the fourth shaft is configured to deliver an additional tool to the distal portion of the first shaft.

11. The device of claim 1, further comprising a cutting device configured to be received within the first lumen and delivered to the distal portion of the first shaft, the cutting device having a proximal-facing cutting surface and/or a distal-facing cutting surface.

12. The device of claim 1 wherein:
    the third shaft is configured to slidably receive a guidewire via the second lumen; and
    the device has a third lumen extending along at least a portion of the first shaft, wherein the third lumen is configured to receive a visualization device.

13. The device of claim 1, further comprising an expandable member carried by the distal portion of the first shaft and spaced longitudinally apart from the plurality of capture members, wherein the first shaft further defines a third lumen coupled to the expandable member.

14. The device of claim 13 wherein the expandable member is a dilation balloon, and wherein the third lumen comprises an inflation lumen in fluid communication with the dilation balloon.

15. The device of claim 13 wherein the expandable member is an expandable cage, and wherein the expandable cage is coupled to a connecting member extending through the third lumen.

16. The device of claim 1 wherein each of the plurality of capture members includes a distal joint at its distal terminus, a proximal joint at its proximal terminus, and an intermediate joint positioned along its length between the distal joint and the proximal joint.

17. The device of claim 16 wherein the proximal movement of the second shaft relative to the first shaft causes a portion of each of the plurality of capture members between the proximal joint and the intermediate joint to bend in a curved, concave direction.

18. The device of claim 16 wherein the proximal movement of the second shaft relative to the first shaft causes a portion of each of the plurality of capture members between the distal joint and the intermediate joint to bend in a curved, concave direction.

19. A device for modifying intraluminal tissue, the device comprising:
    a first shaft having a proximal portion and a distal portion, the first shaft comprising—
        a first lumen extending between the proximal portion and the distal portion; and
        a plurality of capture members extending along a length of the distal portion, wherein each of the plurality of capture members includes a distal joint coupled to the first shaft, a proximal joint coupled to the first shaft, and an intermediate joint positioned between the distal joint and the proximal joint;
    a second shaft disposed within the first lumen, wherein a distal end region of the second shaft is fixed to a distal end region of the first shaft such that proximal movement of the first shaft with respect to the second shaft pulls the distal joint of each of the plurality of capture members proximally and causes the plurality of capture members to bend outwardly away from a central axis of the first shaft; and
    a third shaft extending along at least a portion of the first shaft, the third shaft including a second lumen configured to deliver a tool along the distal portion of the first shaft.

20. The device of claim 19 wherein the second lumen merges with the first lumen distal to the plurality of capture members of the first shaft.

21. The device of claim 19 wherein the second lumen is configured to receive a guidewire therethrough to control a position of the device while the plurality of capture members are in an expanded state.

22. The device of claim 19 wherein the third shaft comprises a visualization section positioned at least partially adjacent to the plurality of capture members to allow an imaging device within the second lumen to image the plurality of capture members.

23. The device of claim 19 wherein the proximal movement of the second shaft with respect to the first shaft causes the distal joint to move to a position proximal to the intermediate joint.

24. The device of claim 19 wherein the proximal movement of the second shaft with respect to the first shaft causes the intermediate joint to move to a position proximal to the proximal joint.

25. The device of claim 19 wherein:
the first shaft further includes a plurality of openings extending through at least a portion of a corresponding one of the plurality of capture members;
the second shaft is configured to slidably receive a cutting device having a plurality of expandable cutting elements; and
when the cutting device is in a deployed state, each of the plurality of expandable cutting elements extends outwardly away from the central axis of the second shaft through a corresponding one of the plurality of openings in the first shaft.

26. A device for modifying intraluminal tissue, the device comprising:
an outer shaft having a proximal portion, a distal portion, a first lumen extending between the proximal portion and the distal portion, and a plurality of slots extending along
a length of the distal portion, wherein—
regions of the outer shaft between the plurality of slots define capture members extending along the length of the distal portion, and
each of the capture members includes a distal joint at a distal terminus, a proximal joint coupled at a proximal terminus, and an intermediate joint positioned between the distal joint and the proximal joint;
an inner shaft disposed within the first lumen, wherein a distal end region of the inner shaft is fixed to a distal end region of the outer shaft such that proximal movement of the inner shaft with respect to the outer shaft causes the capture members to actuate outwardly away from a central longitudinal axis of the outer shaft; and
an additional shaft extending parallel to at least a portion of the outer shaft, the additional shaft including a second lumen.

27. The device of claim 26 wherein the second lumen has a junction with the first lumen at a location distal to the capture members of the outer shaft.

28. The device of claim 26 wherein the third shaft is configured to slidably receive an imaging device via the second lumen, and wherein a section of the third shaft adjacent to the capture members includes at least one window configured to allow the imaging device to image the capture members as they are actuated.

* * * * *